United States Patent
Leu et al.

(10) Patent No.: US 7,928,188 B2
(45) Date of Patent: Apr. 19, 2011

(54) ANTIGEN POLYPEPTIDE FOR THE DIAGNOSIS AND/OR TREATMENT OF OVARIAN CANCER

(75) Inventors: Sy-Jye Leu, Taipei (TW); Neng-Yao Shih, Tainan (TW); Yi-Yuan Yang, Taipei (TW); Ko-Jiunn Liu, Tainan (TW); I-Jen Huang, Tainan (TW); Yuan-Soon Ho, Taipei (TW); Suparat Charoenfuprasert, Taipei (TW); Yu-Ching Lee, Taipei (TW)

(73) Assignee: Taipei Medical University, Taipei (TW)

( * ) Notice: Subject to any disclaimer, the term of this patent is extended or adjusted under 35 U.S.C. 154(b) by 121 days.

(21) Appl. No.: 12/262,085

(22) Filed: Oct. 30, 2008

(65) Prior Publication Data

US 2010/0111956 A1 May 6, 2010

(51) Int. Cl.
*C07K 7/00* (2006.01)
(52) U.S. Cl. .................. 530/324; 530/350; 435/975
(58) Field of Classification Search .................. None
See application file for complete search history.

(56) References Cited

U.S. PATENT DOCUMENTS

| 4,921,790 | A | 5/1990 | O'Brien | |
| 6,638,721 | B2 * | 10/2003 | Meyers et al. | 506/9 |
| 7,112,426 | B2 * | 9/2006 | Bandman et al. | 435/194 |
| 7,205,146 | B1 * | 4/2007 | Keith et al. | 435/325 |
| 2005/0272061 | A1 * | 12/2005 | Petroziello et al. | 435/6 |

FOREIGN PATENT DOCUMENTS

WO   WO 2005/010148   *   2/2005

OTHER PUBLICATIONS

Mashuho, et al, Interaction of Monoclonal Antibodies with Cell Surface Antigens of Human Ovarian Carcinomas, Journal, Jul. 1984, pp. 2813-2819, Cancer Research, vol. 44.

Steinmeyer, et al, The Expression of hCG Receptor mRNA in Four Human Ovarian Cancer Cell Lines Varies Considerably Under Different Experimental Conditions, Journal, 2003, pp. 13-22, Tumor Biology, vol. 24.

Bast, et al., A Radioimmunoassay Using A Monoclonal Antibody To Monitor The Course Of Epithelial Ovarian Cancer, Journal, Oct. 13, 1983, New England Journal of Medicine, vol. 39, No. 15.

* cited by examiner

*Primary Examiner* — Sheela J Huff
(74) *Attorney, Agent, or Firm* — WPAT, P.C.; Anthony King

(57) ABSTRACT

The invention provides an isolated antigen polypeptide that can be expressed in a subject with ovarian cancer. Also provided is the diagnosis of ovarian cancer by using the antigen polypeptide of the invention and the prevention and/or treatment of ovarian cancer by suppressing the gene of the antigen polypeptide of the invention.

5 Claims, 13 Drawing Sheets

RT-PCR

Western blot

SKOV-3

SKOV-3 sh-OVTA1

ANTIGEN POLYPEPTIDE FOR THE DIAGNOSIS AND/OR TREATMENT OF OVARIAN CANCER

FIELD OF THE INVENTION

The invention provides an isolated antigen polypeptide that can be expressed in a subject with ovarian cancer. Also provided is the diagnosis of ovarian cancer by using the antigen polypeptide of the invention and the prevention and/or treatment of ovarian cancer by suppressing the gene of the antigen polypeptide of the invention.

BACKGROUND OF THE INVENTION

Ovarian cancer is the leading cause of cancer deaths in women worldwide and causes more deaths than all other gynecologic malignancies combined. All women are at risk for ovarian cancer, but older women are more likely to get the disease than younger women. About 90 percent of women who get ovarian cancer are older than 40 years of age, with the greatest number being 55 years or older. Although ovarian cancer remains the number one killer of women with gynecologic malignant hyperplasia, when ovarian cancer is found in its early stages, treatment is most effective. However, ovarian cancer does not cause many symptoms in its early stages. This is why most cases are not found until the cancer has spread. Ovarian cancer at its early stages (I/II) is difficult to diagnose; when it spreads and advances to later stages (III/IV), diagnosis is easier. This is due to the fact that most of the common symptoms are non-specific. Approximately 75% of women diagnosed with such cancer are already at the advanced stages (III and IV) of the disease at their initial diagnosis.

The serum BHCG level should be measured in any female in whom pregnancy is a possibility (Christoph Steinmeyer, Tumor Biol 2003; 24:13-22). Moreover, serum alpha-fetoprotein (AFP) and lactate dehydrogenase (LDH) should be measured in young girls and adolescents with suspected ovarian tumors because the younger the patient, the greater the likelihood of a malignant germ cell tumor. However, outside the aforementioned collection of substances, there has been a relative dearth of antigens which are useful in diagnosis and monitoring; this has been proven particularly true with respect to gynecologic malignancies, especially ovarian carcinomas, which frequently spread throughout the pelvic cavity before diagnosis of the condition. Many of these carcinomas typically exhibit a very aggressive growth pattern and generally respond well to chemotherapy. Thus, an accurate method by which early diagnosis of these diseases could be obtained is highly desirable.

A discovery (Bast, et al., N. Engl. J. Med. 309: 883 [1983]) of a serous cystadinocarcinoma ovarian antigen, known as CA125, has been found to be of significant value in monitoring patients with ovarian cancer. This antigen was isolated by using a monoclonal antibody, OC125, made by stimulation of mice with ovarian cancer cell line OVCA 433. It has been shown to recognize cell surface antigens of the OVCA 433 cell as well as 13 of 14 other ovarian cancer cell lines and a melanoma cell line. The antigen is a high molecular weight (>200,000 daltons) glycoprotein which has been partially purified from tissue culture medium (Masuko, et al., Cancer Res. 44: 2813, 1984). Furthermore, U.S. Pat. No. 4,921,790 relates to a 40 kilodalton subunit of serous cystadinocarcinoma ovarian tumor associated antigen CA125, useful in the diagnosis and monitoring of ovarian cancer. Although a blood test called CA-125 is useful in differential diagnosis and in follow-up on the disease, it has not been shown to be an effective method of screening for early-stage ovarian cancer due to its unacceptably low sensitivity and specificity. Elevated levels of serum CA125 alone or in combination with other known indicators, however, do not provide a definitive diagnosis of malignancy, or of a particular malignancy such as ovarian carcinoma.

Current research is looking at ways to combine tumor marker proteomics with other indicators of disease (i.e., radiology and/or symptoms) in order to improve accuracy. The challenge in such an approach is that the very low population prevalence of ovarian cancer means that even testing with very high sensitivity and specificity will still lead to a number of false positive results (i.e., performing surgical procedures in which cancer is not found). However, the contributions of proteomics are still in the early stages and require further refining. Current studies on proteomics mark the beginning of a paradigm shift towards individually tailored therapy. Currently, neither diagnosis nor five-year survival has greatly improved for these patients. This is substantially due to the high percentage of advanced-stage initial detection of the disease. Therefore, the challenge of developing new detection technology to improve early diagnosis and reduce the percentage of advanced-stage initial diagnoses still exists.

SUMMARY OF THE INVENTION

The invention provides an isolated antigen polypeptide expressed in a subject with ovarian cancer, selected from the group consisting of: (a) a polypeptide comprising an amino acid sequence having at least 85% sequence identity with SEQ ID NO:2; (b) a polypeptide that is encoded by a polynucleotide that hybridizes under stringency conditions with SEQ ID NO: 1 or a full-length complementary strand of SEQ ID NO: 1; (c) a polypeptide encoded by a polynucleotide comprising a nucleotide sequence having at least 85% sequence identity with SEQ ID NO: 1; and (d) a polypeptide comprising an amino acid fragment encoded by a polynucleotide as shown in SEQ ID NO: 4 or comprising an amino acid fragment as shown in SEQ ID NO: 3, provided that the sequence of the polypeptide is included within (a), (b) or (c).

The invention also provides a polynucleotide encoding the isolated antigen polypeptide of the invention.

The invention further provides an antibody specifically binding to a sequence comprising at least the consensus sequence $X_1$-P-H-$X_2$-Y-$X_3$-$X_4$ contained in the C-terminal of the antigen polypeptide of the invention.

The invention further provides a kit for the detection of ovarian cancer in a subject comprising the antibody of the invention.

The invention further provides a method for the diagnosis of the presence of an ovarian cancer in a subject comprising: detecting the expression of the antigen polypeptide of the invention in a biological sample from a subject, under conditions and for a time sufficient to detect the said expression, wherein the expression of the said antigen polypeptide represents the presence of an ovarian carcinoma and the overexpression of the said antigen polypeptide represents the presence of not only an ovarian cancer but also metastasis of the ovarian cancer.

The invention also further provides a method for the diagnosis of ovarian cancer in a subject comprising contacting a biological sample from a subject with the antibody of the invention, to determine the presence in the biological sample of the antigen polypeptide of the invention, under conditions and for a time sufficient to detect binding of the antibody to the consensus sequence, wherein the binding represents the presence of an ovarian cancer. The invention also further provides a method for the prevention and/or treatment of ovarian cancer, comprising the step of suppressing the expression of the antigen polypeptide of the invention.

BRIEF DESCRIPTION OF THE DRAWINGS

In FIG. 4, four radiolabelled bands in total were detected, and it was found that 4.5-kb transcript was the major one in all the ovarian cancer cell lines tested.

FIG. 8 shows that the over-expression of OVTA1 significantly increases cell proliferation and cell migration in OVCAR3 cells.

FIG. 10 shows that the knockdown of OVTA1 significantly reduced cell growth and cell migration in SKOV-3 cells.

FIG. 11 shows that OVTA1 expression is correlated with tumor progression.

DETAILED DESCRIPTION OF THE INVENTION

Figure 1:
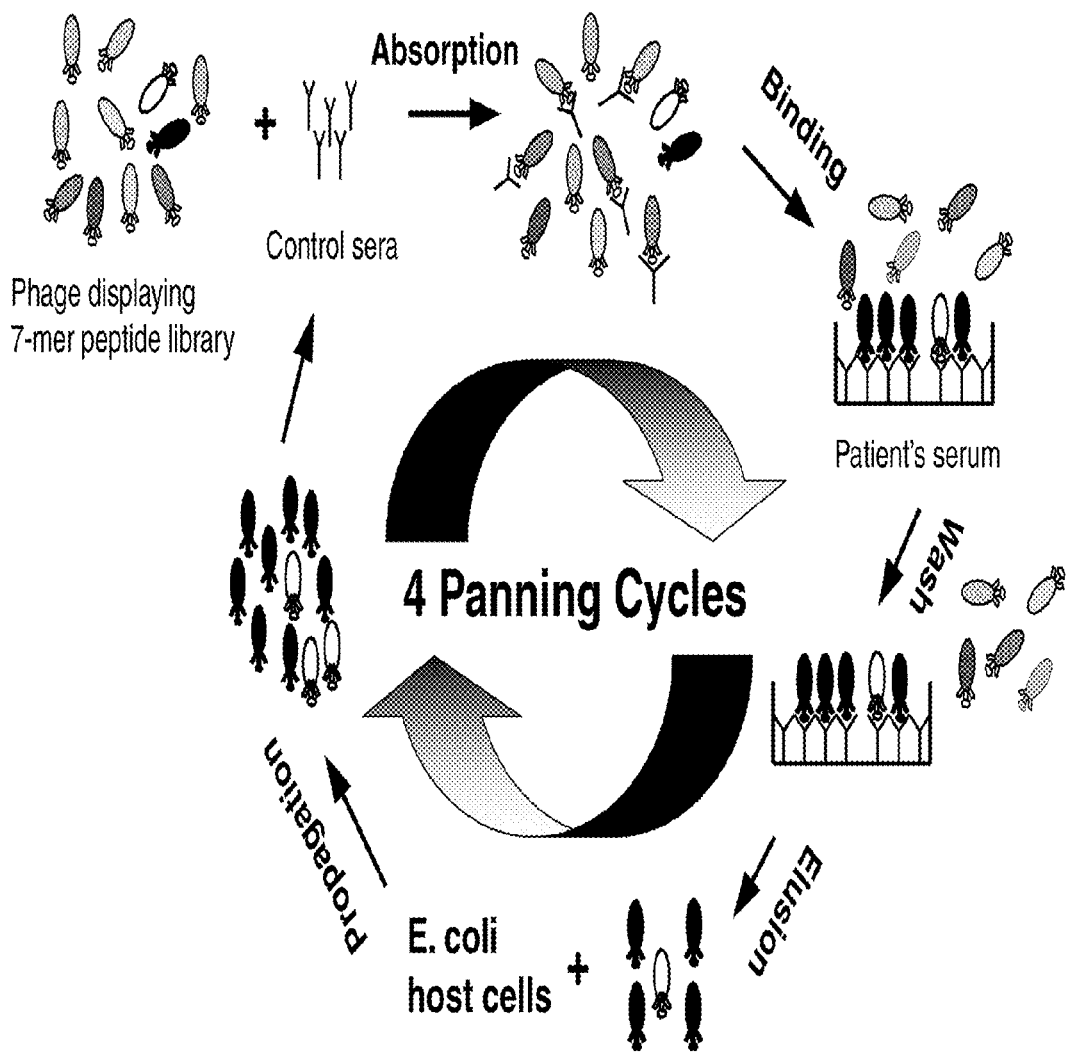
FIG. 1 shows serological identification of ovarian cancer tumor-associated peptides. Serological identification of ovarian tumor-associated antigen genes was carried out using a modified phage display technology. An M13 phage library was applied in which each phage displayed various 7-mer random peptides. The library was pre-absorbed with immunoglobulin IgGs purified from the sera of 30 healthy donors, including 15 males and 15 females, to mask and remove immunogenic epitopes recognized by the normal antibodies. Thereafter, the unbound phages were panned against antibodies purified from 32 patients with ovarian cancer. Bio-panning screening to enrich phages displaying the tumor-associated peptides is schematically shown in FIG. 1. Selection of potential tumor-associated peptides from the resulting library was performed by coating with individual purified ascetic or serum antibody in each well of ELISA plates.

The lack of good diagnostic markers allowing early detection of the disease is one of the causes of the low survival rate of ovarian cancer patients. Further compounding this difficulty in early diagnosis is the lack of effective treatments for ovarian cancer, development of which has been impeded by a deficit in the general understanding of ovarian cancer biology. The invention overcomes these deficits in the art by providing an ovarian tumor marker (OVTA1) that is expressed by OVTA1 gene. The diagnosis of ovarian cancer using OVTA1 of the invention possesses high specificity and sensitivity. Furthermore, the knockdown of OVTA1 can inhibit ovarian tumor cell growth and migration, suggesting that it can be a target for treating ovarian cancer.

Definitions

The term "variant" as used herein means an isoform, an allelic variant of a gene or a region thereof, a naturally occurring mutant form of a gene or a region thereof, or a polypeptide or fragment having an amino acid sequence that differs in one or more amino acids but which retains one or more aspects of the desired characteristic biological function. This may be achieved by the addition of one or more amino acids to an amino acid sequence, the deletion of one or more amino acids from an amino acid sequence and/or the substitution of one or more amino acids for another amino acid or amino acids. Inversion of amino acids and any other mutational change that results in alteration of an amino acid sequence are also encompassed. A variant may be prepared by introducing nucleotide changes in a nucleic acid sequence so that the desired amino acid changes are achieved upon expression of the mutated nucleic acid sequence, or, for instance, by synthesizing an amino acid sequence incorporating the desired amino acid changes, which is well within the capability of the skilled persons.

The term "OVTA1 gene" as used herein means the full-length gene with nucleotides 438 to 4229 (SEQ ID NO:1) of the sequence that is located under Genbank accession number: AB023216. This sequence "AB023216" and its protein product "KIAA0999" (Product ID: 06551) were disclosed in DNA Res. 1999 Feb. 26; 6(1):63-70, whereas its coding gene sequence, the functional protein encoded therefrom and their functions have not been identified yet.

The term "OVTA1 protein" as used herein means the whole sequence of the protein encoded by the OVTA1 gene and its amino acid sequence is shown in SEQ ID NO:2.

The term "isolated" as used herein means that the material is removed from its original environment (e.g., the natural environment if it is naturally occurring). For example, a naturally occurring polypeptide or polynucleotide present in a living animal is not isolated, but the same polypeptide or polynucleotide, separated from some or all of the co-existing materials in the natural system, is isolated. Such polypeptides or polynucleotides can be part of a composition and still be isolated if such composition is not part of its natural environment.

The term "polypeptide" as used herein means a linear series of amino acids connected to one another by peptide bonds between the alpha-amino and carboxy groups of adjacent amino acids.

The term "polynucleotide" or "nucleotide" means polynucleotides comprising DNA. The polynucleotides of the embodiments also encompass all forms of sequences including, but not limited to, single-stranded forms, double-stranded forms, hairpins, stem-and-loop structures, and the like.

The terms "encoding" and "encoded" mean that the polynucleotide or nucleic acid comprises the requisite information for direct translation of the nucleotide sequence into a specified protein. The information by which a protein is encoded is specified by the use of codons. A nucleic acid or polynucleotide encoding a protein may comprise non-translated sequences (e.g., introns) within translated regions of the nucleic acid or may lack such intervening non-translated sequences (e.g., as in cDNA).

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The term "ovarian cancer" as used herein includes primary and metastatic ovarian carcinoma. Criteria for classification of a malignancy as ovarian carcinoma are well known in the art (see Bell et al., 1998 Br. J. Obstet. Gynaecol. 105:1136; Meier et al., 1997 Anticancer Res. 17(4B):3019; Cioffi et al., 1997 Tumori 83:594) as are the establishment and characterization of human ovarian carcinoma cell lines from primary and metastatic tumors (e.g., OVCAR-3, Amer. Type Culture Collection, Manassas, Va.; Yuan et al., 1997 Gynecol. Oncol. 66:378).

The term "antibodies" as used herein includes polyclonal antibodies, monoclonal antibodies, and fragments thereof as well as any naturally occurring or recombinantly produced binding partners, which are molecules that specifically bind the antigen polypeptide of the invention. Antibodies are defined as "immunospecific" or specifically binding if they bind the antigen polypeptide of the invention with a high affinity. Affinities of binding partners or antibodies can be readily determined using conventional techniques, for example, those described by Scatchard et al., Ann. N.Y. Acad. Sci. 51:660 (1949).

The term "expression" as used herein includes any step involved in the production of the polypeptide including, but not limited to, transcription, post-transcriptional modification, translation, post-translational modification, and secretion.

The term "expression vector" as used herein refers to a linear or circular DNA molecule which comprises a polynucleotide encoding a polypeptide of the invention, and which is operably linked to additional nucleotides that provide for its expression. The term "operably linked" denotes a configuration in which a control sequence is placed at an appropriate position relative to the coding sequence of the polynucleotide sequence so that the control sequence directs the expression of the coding sequence of a polypeptide.

The term "host cell" as used herein includes any cell type which is susceptible to transformation, transfection, transduction, and the like with a nucleic acid construct comprising a polynucleotide of the present invention.

The term "identity" as used herein refers to the relatedness between two amino acid sequences or between two nucleotide sequences. For the purposes of the present invention, the degree of identity between two amino acid sequences or two nucleotide sequences is determined by the known methods and software. For example, Clustal method (Higgins, 1989, CABIOS 5: 151-153) or the Wilbur-Lipman method (Wilbur and Lipman, 1983, Proceedings of the National Academy of Science USA 80: 726-730).

Antigen Polypeptide of the Invention and Polynucleotides Encoding the Same

The invention is the first to unexpectedly discover the antigen polypeptide (OVTA1 protein) encoded by OVTA1 gene that can be expressed in a subject with ovarian cancer. The above-mentioned antigen polypeptide is named an ovarian tumor-associated antigen. By detecting the existence of the antigen polypeptide (OVTA1 protein) in a subject, the ovarian cancer can be diagnosed.

The invention provides an isolated antigen polypeptide expressed in a subject with ovarian cancer, selected from the group consisting of: (a) a polypeptide comprising an amino acid sequence having at least 85% sequence identity with SEQ ID NO:2; (b) a polypeptide that is encoded by a polynucleotide that hybridizes under stringency conditions with SEQ ID NO: 1 or a full-length complementary strand of SEQ ID NO: 1; (c) a polypeptide encoded by a polynucleotide comprising a nucleotide sequence having at least 85% sequence identity with SEQ ID NO: 1; and (d) a polypeptide comprising an amino acid fragment encoded by a polynucleotide as shown in SEQ ID NO: 4 or comprising an amino acid fragment as shown in SEQ ID NO: 3, provided that the sequence of the polypeptide is included within (a), (b) or (c).

In a first aspect, the invention relates to isolated polypeptides having an amino acid sequence which has a degree of identity to SEQ ID NO: 2 of at least 85%, preferably at least 90%, more preferably at least 95%, and most preferably at least 98%, and which can be expressed in a subject with ovarian cancer.

A polypeptide of the present invention preferably comprises the amino acid sequence of SEQ ID NO: 2, a variant thereof, or a fragment thereof that can be expressed in a subject with ovarian cancer. According to the invention, the variant of the invention may be artificial variants comprising a conservative substitution, deletion, and/or insertion of one or more amino acids of SEQ ID NO: 2 or the mature polypeptide thereof. Preferably, amino acid changes are of a minor nature, that is, they are conservative amino acid substitutions or insertions that do not significantly affect the folding and/or activity of the protein. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

According to a further embodiment of the invention, the antigen polypeptide of the invention comprises the amino acids shown in SEQ ID NO:2.

In a second aspect, the present invention relates to isolated polypeptides expressed in a subject with ovarian cancer which are encoded by polynucleotides which hybridize under stringency conditions, preferably moderate stringency conditions, more preferably high stringency conditions, and most preferably very high stringency conditions with nucleotides shown in SEQ ID NO: 1 or a full-length complementary strand of SEQ ID NO: 1 (J. Sambrook, E. F. Fritsch, and T. Maniatus, 1989, Molecular Cloning, A Laboratory Manual, 2nd edition, Cold Spring Harbor, N.Y.). The conditions of temperature and ionic strength determine the "stringency" of the hybridization. For preliminary screening for homologous nucleic acids, low stringency hybridization conditions, corresponding to a $T^m$ (melting temperature) of 55° C., can be used, e.g., 5 times SSC, 0.1% SDS, 0.25% milk, and no formamide; or 30% formamide, 5 times SSC, 0.5% SDS. Moderate stringency hybridization conditions correspond to a higher $T^m$, e.g., 40% formamide, with 5 times or 6 times SCC. High stringency hybridization conditions correspond to the highest $T^m$, e.g., 50% formamide, 5 times or 6 times SCC. SCC is a 0.15M NaCl, 0.015M Na-citrate.

In a third aspect, the present invention relates to the isolated polypeptide expressed in a subject with ovarian cancer which is a polypeptide encoded by a polynucleotide comprising a nucleotide sequence having at least 85% sequence identity, preferably at least 90%, more preferably at least 95%, and most preferably at least 98%, which can be expressed in a subject with ovarian cancer, with the nucleotides shown in SEQ ID NO: 1.

According to one embodiment of the invention, the antigen polypeptide of the invention can be encoded by the nucleotide sequence shown in SEQ ID NO:1 or its degenerate sequence. According to a further embodiment of the invention, the antigen polypeptide of the invention can be encoded by the nucleotide sequence shown in SEQ ID NO:1.

In a fourth aspect, the invention relates to the isolated polypeptides expressed in a subject with ovarian cancer, which comprise an amino acid fragment encoded by a polynucleotide as shown in SEQ ID NO: 4 or an amino acid fragment as shown in SEQ ID NO: 3, provided that the sequence of the polypeptide is included within (a), (b) or (c). The invention also unexpectedly finds that the polypeptides having an amino acid fragment 955 to 1112 (SEQ ID NO:3) of OVTA1 protein possess better immunogenic activity and can also be used as an ovarian tumor-associated antigen. The above-mentioned polypeptides are encoded by the nucleotides 2863 to 3336 (SEQ ID NO:4) of OVTA1 gene.

The techniques used to isolate or clone a polynucleotide encoding a polypeptide of the invention are known in the art and include isolation from genomic DNA, preparation from cDNA, or a combination thereof. The cloning of the polynucleotides of the present invention from such genomic DNA can be effected by, for example, using the well-known polymerase chain reaction (PCR) or antibody screening of expression libraries to detect cloned DNA fragments with shared structural features. Other nucleic acid amplification procedures such as ligase chain reaction (LCR), ligated activated transcription (LAT) and nucleotide sequence-based amplification (NASBA) can be used.

The antigen polypeptide of the invention may be prepared by processes well known to those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques. Therefore, the invention also relates to nucleic acid constructs comprising an isolated polynucleotide of the present invention operably linked to one or more control sequences which direct the expression of the coding sequence in a suitable host cell under conditions compatible with the control sequences. An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

For production of the antigen polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., BASIC METHODS IN MOLECULAR BIOLOGY (1986) and Sambrook, et al., MOLECULAR CLONING: A LABORATORY MANUAL, 2nd Ed., Cold Spring Harbor Laboratory Press, Cold Spring Harbor, N.Y. (1989). Representative examples of appropriate hosts include bacterial cells, such as cells of E. coli (JM109 strain).

A great variety of expression systems can be used to produce the polypeptides of the invention. Such vectors include, among others, chromosomal-, episomal- and virus-derived vectors. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL (suppl).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

The expressed antigen polypeptide of the invention may also be useful as target antigens in any of a number of assay configurations for routine antibody screening, which can be readily performed by those having ordinary skill in the art.

Antibodies Specific to the Antigen Polypeptide of the Invention

The invention provides an antibody specifically binding to a sequence comprising at least the consensus sequence $X_1$-P-H-$X_2$-Y-$X_3$-$X_4$ contained in the C-terminal of the antigen polypeptide of the invention, wherein $X_1$, $X_2$, $X_3$ and $X_4$ can be any amino acid. Preferably, $X_1$ can be Q, N, S, T, V, W, A or L; $X_2$ can be H, S, G or N; $X_3$ can be S, P, M, F, A or K and $X_4$ can be L, H, K, F, M, S or R. More preferably, the consensus motif has the amino acid sequence Thr-Pro-His-Gly-Tyr-Ala-His (SEQ ID NO:5). The invention finds that the antigen polypeptide contains a consensus motif, $X_1$-P-H-$X_2$-Y-$X_3$-$X_4$, which is a highly immunogenic epitope for an antibody. According to one preferred embodiment of the invention, the antibody of the invention specifically binds to the antigen polypeptide of the invention. More preferably, the antibody of the invention specifically binds to SEQ ID NO:2 or SEQ ID NO: 3 of the invention.

Antibodies that are specific for the consensus sequence of the antigen polypeptide of the invention are readily generated as monoclonal antibodies or as polyclonal antisera, or may be produced as genetically engineered immunoglobulins (Ig) that are designed to have desirable properties using methods well known in the art. The polyclonal antibody can be obtained by purifying the obtained antiserum through an optional combination of known purification methods such as salting out, ion exchange chromatography, affinity chromatography and the like. The monoclonal antibody can be obtained in the following manner. Antibody producing cells such as splenocytes, lymphocytes or the like are collected from the immunized animal and fused with myeloma cells or the like to make them into hybridoma cells by a known method in which polyethylene glycol, Sendai virus, an electric pulse or the like is used. Thereafter, a clone capable of producing an antibody which binds to the consensus sequence of the antigen polypeptide of the invention is selected and cultured, and the monoclonal antibody of interest is purified from the resulting culture supernatant. The purification may be effected through an optional combination of known purification methods such as salting out, ion exchange chromatography, affinity chromatography and the like. The novel antibody can also be obtained by means of genetic engineering techniques. That is, mRNA is isolated from splenocytes or lymphocytes of an animal which is immunized with the consensus sequence of the antigen polypeptide of the invention or from a hybridoma capable of producing a monoclonal antibody which is specific for the consensus sequence of the antigen polypeptide of the invention, and a cDNA library is prepared using the isolated mRNA. Thereafter, a clone capable of producing an antibody which reacts with the consensus sequence of the antigen polypeptide of the invention is screened from the cDNA library and cultured to obtain a culture supernatant from which the antibody of interest is purified through a combination of known purification methods. For example, by way of illustration and not limitation, antibodies may include recombinant IgGs, chimeric fusion proteins having immunoglobulin derived sequences or "humanized" antibodies that may all be used for detection of the OVTA1 according to the invention.

Kits Comprising Antibodies that Bind to a Sequence Comprising at least the Consensus Sequence of the Antigen Polypeptide of the Invention The invention also provides kits comprising the isolated antigen polypeptide of the invention or antibodies that bind to a sequence comprising at least the consensus sequence of the antigen polypeptide of the invention, for use in diagnosis of ovarian cancer. Accordingly, the kits comprise an isolated antigen polypeptide of the invention or an antibody that can bind to a sequence comprising at least the consensus sequence of the antigen polypeptide of the invention specifically and/or form a complex with the sequence. More preferably, the antigen polypeptide of the invention has the amino acid sequence as shown in SEQ ID NO: 2 or SEQ ID NO:3 and the antibody of the invention specifically binds to SEQ ID NO:2 or SEQ ID NO: 3 of the invention. The binding of an antibody (e.g., monoclonal, polyclonal, human, humanized, etc.) is used for diagnosing ovarian cancer in an individual. The kits of this invention are in suitable packaging, and optionally provide additional components such as buffers and instructions for determining binding to a sequence comprising at least the consensus sequence of the antigen polypeptide of the invention, such as capture reagents, developing reagents, labels, reacting surfaces, means for detection, control samples, and interpretive information. The instructions may be for any measurement of antigen binding, including, but not limited to, those assays described herein. In some embodiments, reagents described above are supplied so that multiple measurements may be made, for example, allowing for measurements in the same individual over time or multiple individuals. Any appropriate means for detecting binding of the antibodies may be employed (and provided in the kits), such as a labeled anti-human antibody, wherein the label may be an enzyme, fluorophore, chemiluminescent material radioisotope or coenzyme. Generally, the label used will be an enzyme.

Methods for Detecting or Diagnosing Ovarian Cancer in a Biological Sample

The invention provides a method for the diagnosis of the presence of an ovarian cancer in a subject comprising: detecting the expression of the antigen polypeptide of the invention in a biological sample from a subject, under conditions and for a time sufficient to detect the said expression.

The invention also provides a method for the diagnosis of ovarian cancer in a subject comprising contacting a biological sample from a subject with at least one antibody specific for a sequence comprising at least the consensus sequence $X_1$-P-H-$X_2$-Y-$X_3$-$X_4$ (preferably Thr-Pro-His-Gly-Tyr-Ala-His) contained in the C-terminal of the antigen polypeptide of the invention, to determine the presence in the biological sample of the antigen polypeptide of the invention, under conditions and for a time sufficient to detect binding of the antibody to the consensus sequence, and therefrom detecting the presence of an ovarian cancer or metastasis of the ovarian cancer. The expression of the said antigen polypeptide represents the presence of an ovarian carcinoma and the over-expression of the said antigen polypeptide represents the presence of not only an ovarian cancer but also metastasis of the ovarian cancer.

According to the invention, the antigen polypeptide of the invention may be detected in a biological sample from a subject or biological source. Biological samples may be provided by obtaining a blood sample, biopsy specimen, tissue explant, organ culture, biological fluid or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like. In certain preferred embodiments of the invention, the subject or biological source may be suspected of having or being at risk for ovarian cancer, and in certain other preferred embodiments of the invention the subject or biological source may be known to be free of a risk or presence of such disease. According to the invention, the biological sample is selected from the group consisting of ovarian tissue, ovarian cell, blood, serum, plasma, ascites fluid, and peritoneal fluid.

According to the invention, the over-expression of the antigen polypeptide of the invention or OVTA1 protein can significantly increase proliferation and migration of ovarian cancer cells. Therefore, the detection of the expression level of the antigen polypeptide of the invention can be used to diagnose ovarian cancer and its metastasis.

Knockdown of OVTA1 for the Treatment of Ovarian Cancer

After further knockdown studies, the invention found that the knockdown of OVTA1 could significantly reduce cell growth and cell migration as well as tumor growth rate. The knockdown of the antigen polypeptide of the invention or OVTA1 can be used in the prevention and/or treatment of ovarian cancer and inhibition of metastasis of ovarian cancer. Accordingly, the invention provides a method for the prevention and/or treatment of ovarian cancer, comprising the step of suppressing the expression of the antigen polypeptide of the invention or OVTA 1.

EXAMPLE

Example 1

Production of the Antigen Polypeptide of the Invention and Confirmation of the Antigen as an Immunogenic Target Cell culture. OVCAR-3, SKOV-3, and TOV-112D ovarian cancer cell lines and HeLa were obtained from American Type Culture Collection (Rockville, Md.). OVCAR-3 and SKOV-3 cells were cultured in DMEM and Ham's F-12 medium (1:1) (Invitrogen, Carlsbad, Calif.) supplemented with 10% fetal bovine serum (FBS), penicillin (100 units/ml)/streptomycin (100 μg/ml), 0.1 mM nonessential amino acids and 1 mM sodium pyruvate (Invitrogen). TOV-112D cells were cultured in MCDB105 and Media 199 (1:1) (Sigma, St. Louis, Mo.) plus 15% FBS, penicillin, and streptomycin. HeLa cells were maintained in DMEM containing 10% FBS.

Ascetic fluids, serum and tissue samples. 12 ascetic fluid and 36 tissue section samples were collected under permission of the Institution Review Board, National Health Research Institute. Histological subtypes of ascetic samples were 10 serous, 1 clear-cell, and 1 mucinous subtypes, while the tissue samples included 16 serous-, 9 endometrioid-, 6 clear-cell, 4 mucious-, and 1 endometrioid/clear cell mix-subtypes. The control sera were obtained from 10 age-matched healthy women. Their immunoglobulin G (IgG) fraction of the ascetic fluid and serum samples was purified with immobilized Protein A/G (Pierce, Rockford, Ill.) according to the manufacturer's instructions.

Screening of phage library. Serological selection of phage clones displaying peptides recognized by malignant ascetic antibodies of patients with ovarian cancer was performed using a Ph.D.-7 phage display peptide system (New England BioLabs, Beverly, Mass.). A bio-panning procedure was carried out according to the manufacturer's instructions with certain modifications. Briefly, after removal of non-specific binders with healthy control IgG mixture, phages ($10^{11}$ pfu) were incubated with a pool of IgG antibodies (100 μg/ml) purified from 32 patients with ovarian cancer which was pre-coated in a 96-well plate for 2 hrs at room temperature. The unbound phages were removed by washing 10 times with TBST solution [50 mM Tris-HCl (pH 7.5), 150 mM NaCl, 0.1% Tween-20]. The bound phages were eluted in an elution buffer [0.2 M Glycine-HCl (pH 2.2), 1 mg/ml BSA] and propagated by infecting E. coli host cell (strain ER 2738) at 37° C. with vigorous agitation for 4-5 hrs. After centrifugation, the cells were discarded. The amplified phages were collected by addition of ⅙ volume of PEG/NaCl solution [20% (w/v) polyethylene glycol-8000, 2.5 M NaCl] to the supernatant followed by centrifugation at 4° C., 16,000×g for 15 min. The resultant phages were re-suspended in TBS [50 mM Tris-HCl (pH 7.5), 150 mM NaCl] and the titers were determined on LB/IPTG/Xgal plates as described in the provided manual. The above bio-panning procedure was repeated 3 more times to enrich the antibody-bound phage clones.

The peptide sequences presented by bound phages were resolved by direct DNA sequencing. Phages from fifteen blue plaques were randomly selected, amplified in E. coli host cells, and collected by precipitation and centrifugation as described above. The resultant pellets were re-suspended in 100 μl Iodide buffer [10 mM Tris-HCl (pH 8.0), 1 mM EDTA, 4 M NaI] containing 250 μl ethanol. After incubation for 10 min, the single-stranded phage DNA was preferentially precipitated and dissolved in 30 μl TE buffer [10 mM Tris-HCl (pH 8.0), 1 mM EDTA]. The DNA inserts coding for displayed peptide was determined by direct sequencing in an automated DNA sequencer ABI 8700.

Enzyme-linked immunosorbent assay (ELISA). Sequence analysis showed that one consensus motif, $X_1$-P-H-$X_2$-Y-$X_3$-$X_4$, was displayed by 87% (13/15) of the selected phage clones. To determine the binding of phage containing Peptide #10 to individual antibodies purified from 12 patients with ovarian cancer, ELISA assay was performed by coating the purified antibodies in each well. After washing, the bound phages were detected by anti-M13 antibody conjugated with horse-radish peroxidase (HRP) (1:2000) and visualized by incubation with ABTS peroxidase substrate (KPL, Caithersburg Md.). The titers of individual samples were measured at $OD_{450}$. The control wells were coated with 10 μg/ml of BSA or 100 μg/ml purified IgG mixture or sera from healthy subjects. M13 phage not displaying any peptide was also included as a negative control.

Gene construction and antiserum generation. The FJ10213 plasmid was served as a gene template for coding for KIAA0999 protein in this study. The gene insert was cut with Sal I and Not I enzymes, blunted, and subcloned into pcDNA3.1 vector at EcoR V, named as pcDNA-FJ10213. On the basis of the gene sequence of FJ10213 available on NCBI GenBank (accession number: AB023216), an myc-tagged plasmid, named myc-CT-OV1, was constructed by cloning the nucleotides 2278 to 3336 of FJ10213 clone into pBlue-Script vector with EcoRI sites. This DNA insert encoded a 353 amino-acid C-terminal partial protein of OVTA1, including the consensus motif, TPHGYAH, recognized by the phage clones. The plasmid myc-CT-OV1 del-7mer lacking the consensus sequence was generated by site-direct mutagenesis using a pair of primers listed below.

Forward primer:
(SEQ ID NO: 6)
5'-GCT TCC TCA CCC ACC CCG CAG CCG GCA CTG ATG CAT-3'

Backward primer:
(SEQ ID NO: 7)
5'-ATG CAT CAG TGC CGG CTG CGG GGT GGG TGA GGA AGC-3'

For generation of an antiserum specific to OVTA1, the nucleotides 2863 to 3336 (SEQ ID NO:4) were cloned into a pGEX-KG vector at 5'-Xba I and 3'-Xho I sites and expressed in *E. coli* (JM109 strain). The GST-tagged recombinant protein was purified as described in a previous study (Clinical Cancer Research, Oct. 1, 2006; 12(19): 5746-5754) and served as an immunization antigen for rabbits or mice. The resultant antisera were purified with Melon gel IgG purification system (Pierce Biotechnology, Inc., IL, U.S.A.) according to the manufacturer's instructions. For functional study in a cell, the full-length OVTA1 gene with nucleotides 438 to 4229 (SEQ ID NO:1) was constructed into a vector, pcDNA3-myc, and expressed as an Myc-OVTA1 recombinant protein. Additionally, a plasmid, named pshOVTA1 (clone number: RHS3979-9604860), expressing small interfering RNA to knockdown OVTA1 level and its scramble control pLKO.1 were obtained from Open Biosystems (Huntsville, Ala., U.S.A.). Stable elevation of OVTA1 gene expression was established in OVCAR-3 cells; meanwhile, attenuation of its expression by transfection of pshOVTA1 was manipulated in SKOV-3 cells.

An attempt was made to select more immunogenic tumor-associated antigens that could be recognized by autoantibodies purified from ascetic fluids of patients with ovarian cancer. A 7-mer random peptide phage display library was used for this screening. The bio-panning experiment for this screening is schematically illustrated in FIG. 1. The library was pre-absorbed with total immunoglobin G (IgG) purified from 30 healthy donors to mask peptide epitopes that were recognized by the IgG. Subsequently, the individual purified ascetic IgG obtained from 32 patients with ovarian cancer was used to select phages displaying potential tumor-associated peptides. After 4 bio-panning enrichment cycles, 13 out of 15 phage clones displayed consensus xPHxYxx sequences as shown in Table 1 below.

TABLE 1

| No. | Peptide sequences | | | | | | | Gene ID |
|---|---|---|---|---|---|---|---|---|
| #1 | Q | P | H | H | Y | S | L | (SEQ ID NO: 8) Rat CL3BA/AA |
| #2 | N | P | H | S | Y | P | H | (SEQ ID NO: 9) N/A |
| #3 | Q | P | H | H | Y | P | L | (SEQ ID NO: 10) N/A |
| #4 | S | P | H | H | Y | P | H | (SEQ ID NO: 11) N/A |
| #5 | T | P | H | H | Y | M | H | (SEQ ID NO: 12) N/A |
| #6 | V | P | H | S | Y | P | H | (SEQ ID NO: 13) N/A |
| #7 | Q | P | H | H | Y | F | K | (SEQ ID NO: 14) N/A |
| #8 | W | P | H | H | F | P | H | (SEQ ID NO: 15) N/A |
| #9 | V | P | H | G | Y | F | L | (SEQ ID NO: 16) Murine L05 |
| #10 | T | P | H | G | Y | A | H | (SEQ ID NO: 17) Human OVTA1 |
| #11 | V | P | H | S | Y | P | H | (SEQ ID NO: 18) N/A |
| #12 | Q | P | H | H | Y | P | F | (SEQ ID NO: 19) N/A |
| #13 | A | P | H | H | Y | P | M | (SEQ ID NO: 20) N/A |
| #14 | L | A | I | N | I | K | S | (SEQ ID NO: 21) N/A |
| #15 | S | P | H | S | Y | P | R | (SEQ ID NO: 22) N/A |

Consensus: $X_1$ P H $X_2$ Y $X_3$ $X_4$

Figure 2:
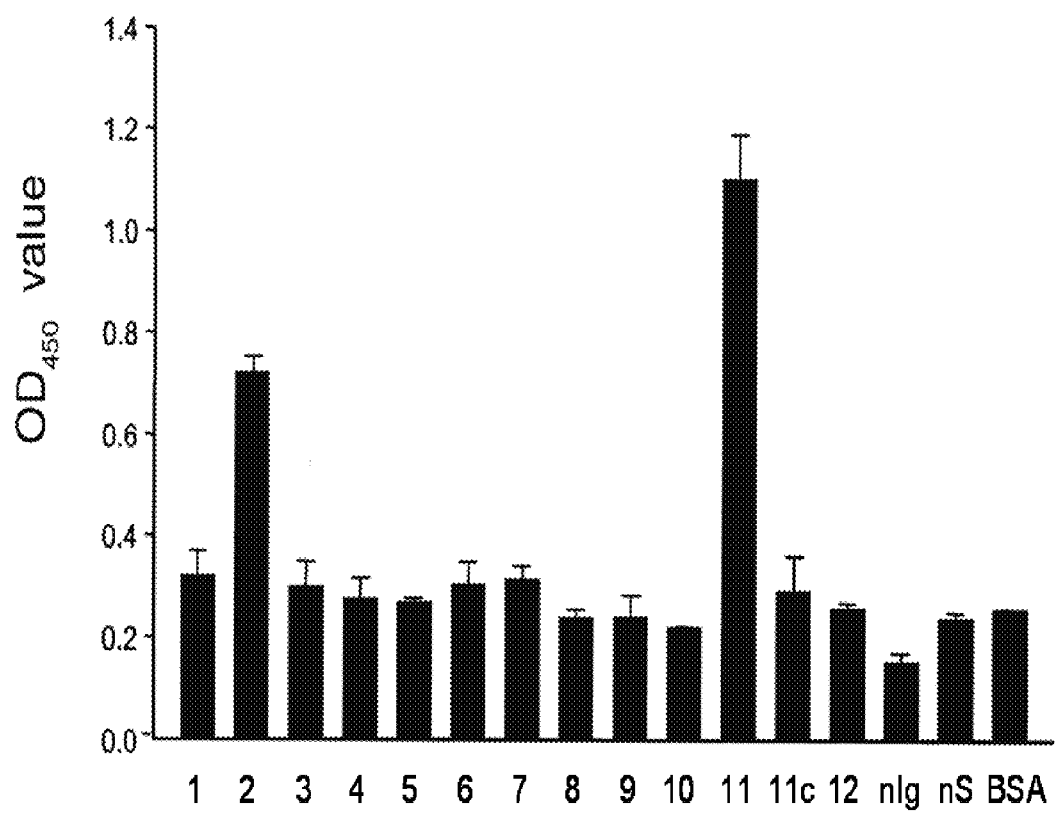
FIG. 2 shows the binding of the phage containing Peptide #10 to antibodies purified from 11 patients with ovarian cancer in ELISA assay (1-12: Ig purified from 12 patients as coating antigens for detecting phage #10; 11c: Ig purified from patient 11 as coating antigen for detecting M13 phage as a control experiment; nIg: Ig purified from 30 normal subjects as coating antigen for detecting phage #10; and nS: normal sera as coating antigen for detecting phage #10). ELISA assay was performed by coating the purified antibody in each well. The bound phages were detected with an antibody specific to M13 phages and visualized by incubating with ABTS, an HRP substrate in the assay. For background control, purified or unpurified serum antibodies or bovine serum albumin were coated onto separated wells. In addition, M13 phage without displaying any peptide was included as a negative control. The results show that the phage with Peptide #10 specifically binds to the antibody purified from patient 11 (CA502).

To reveal displayed peptides of antibody-bound phages, the inserted nucleotide sequences of coding for the displayed peptides were directly sequenced. As a result, the displayed peptide sequences of 15 randomly chosen antibody-bound phages after $4^{th}$ panning are deduced and listed in Table 1. Intriguingly, one consensus motif, $X_1PHX_2YX_3X_4$, was obtained from those displayed peptide sequences. Putative proteins, found in a search of NCBI protein database, containing those displayed peptide sequences are indicated in the right column of Table 1. Among them, one human novel gene containing Peptide #10 is temporarily named OVTA1 gene, which was previously identified as KIAA0999 gene. The putative polypeptide encoded by KIAA0999 gene contains Pro-His-Gly-Tyr-Ala-His sequence. Thus, it suggests that displayed peptide sequences by those phages may be associated with tumor antigens. In addition, the data shown in FIG. 2 indicates that the phage clone displaying peptide TPH-GYAH can strongly bind to ascetic antibodies purified from ovarian cancer patient 11 (CA502).

Figure 3:
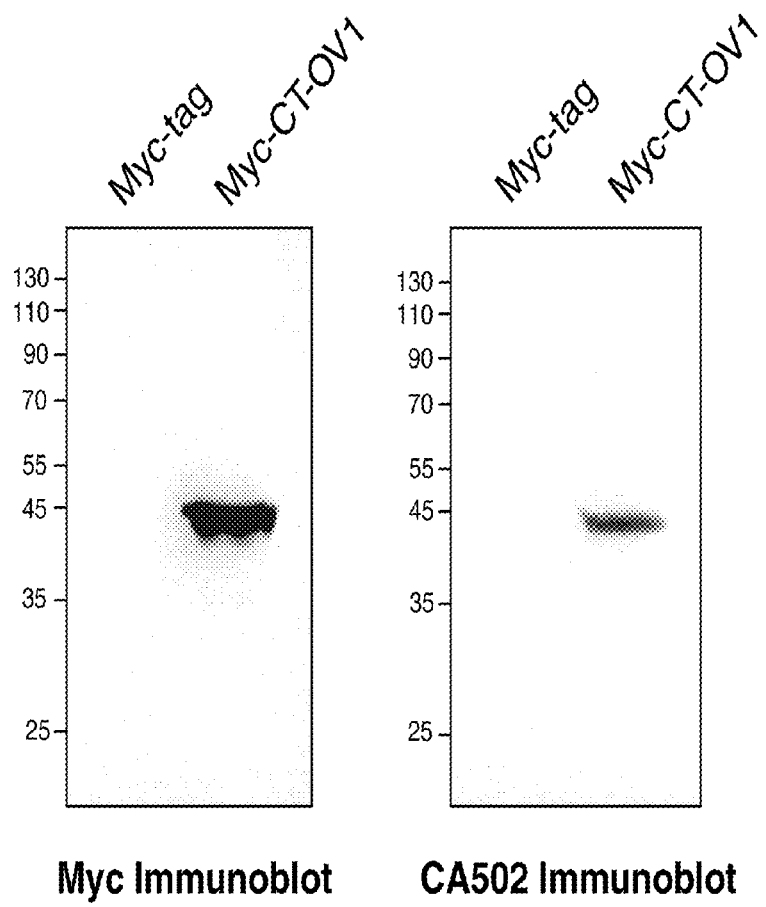
FIG. 3 shows the confirmation of OVTA1 as an antigenic target of CA502 antibodies. To confirm that OVTA1 was an antigenic target of CA502 antibody, C-terminus (CT) of the putative gene was cloned out from a human fetal brain cDNA library, expressed as an myc-tagged protein in HeLa cells, and probed with CA502 antibody. Western blot analysis shown in FIG. 3A clearly demonstrated positive immunoreactivity of CA502 antibody to the C-terminus that contains Peptide #10 sequence, TPHGYAH. To further examine whether this peptide is an immunogenic epitope of CA502 antibody, site-directed deletion mutagenesis was performed. Deletion of the peptide from the C-terminus resulted in loss of immunoreactivity of CA502 antibody (FIG. 3B), indicating that the random-peptide phage displaying system is a powerful tool for screening immunogenic epitope(s) of an antigen.
Figure 3:
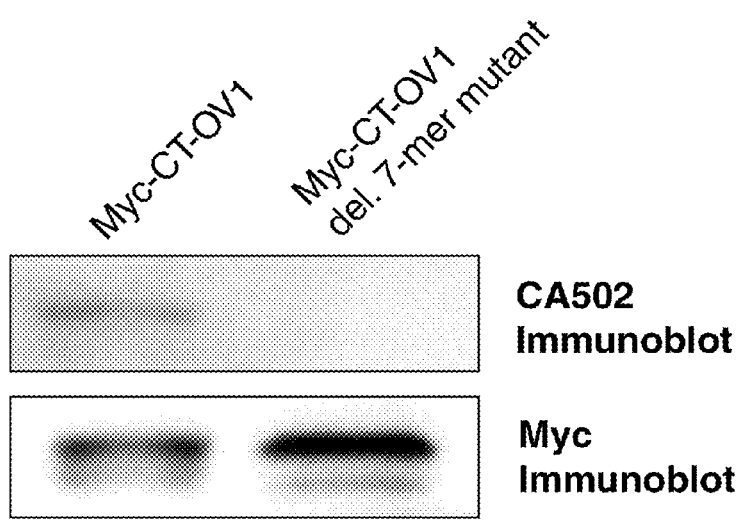

Serological confirmation of the antigen polypeptide of the invention as an immunogenic target. To verify that the antigen polypeptide of the invention was the immunogenic target of Patient 11's (CA502) ascetic antibody, a putative 3'-coding region of OVTA1 gene coding for an Myc-tagged 40 KDa polypeptide containing the Pro-His-Gly-Tyr-Ala-His sequence was cloned out from SK-OV3 cells. Western blotting analyses (see Example 2 below) of HeLa cells overexpressing the putative C-terminal OVTA1 (CT-OVTA1) gene tagged with myc sequence and probed with either purified Patient 11 or anti-Myc antibodies indicated that the Peptide #10 containing C-terminus of the invention was indeed an immunogenic target of Patient 11's ascetic autoantibody (FIG. 3A). To further confirm whether the Pro-His-Gly-Tyr-Ala-His sequence was the major immunogenic epitope for the antibody, a deletion mutant lacking this particular sequence displayed by the cloned phages was generated. Intriguingly, removal of the sequence totally abolished recognition of the Patient autoantibody to the antigen polypeptide of the invention (FIG. 3B), suggesting that this particular sequence in the antigen polypeptide of the invention is one of the highly immunogenic epitopes for tumor immunosurveillance.

Example 2

Expression of the Antigen Polypeptide of the Invention

Western blot analysis. The cell lysates were prepared as described in a previous study (BMC Molecular Biology 2007, 8:72 pp. 1-15). The cells were transfected with a plasmid coding for wild-type, mutant KIAA0999 gene, or control vector using Lipofectamine (Invitrogen Co., CA, U.S.A.) for HeLa cells or Lipofectamine 2000 transfect reagent for OVCAR-3 and SKOV-3 cells according to the manufacturer's instructions. After 24 hrs transfection, cells were lysed in a lysis buffer [20 mM Tris-HCl, 150 mM NaCl, 0.1% SDS, 5 mM $MgCl_2$, 10% glycerol, 0.5% NP-40, 100 mM NaF, 1 M $Na_3VO_4$, and protease inhibitor cocktail (Roche Diagnostics, Indianapolis, Ind., U.S.A.)]. The protein concentration was quantified using BCA protein assay (Pierce). Approximately 15 or 150 µg of each sample was resolved in 7.5-10% SDS-PAGE, transferred to nitrocellulose membrane, and blotted with an antibody specific to myc-tag (1:10,000 dilution), GST-tag (1:1,000 dilution) (Pierce), OVTA1 (1:1,000 dilution), or with CA502 purified ascetic antibody (32 µg/ml). The immuno-complexes were detected by probing with anti-mouse, -rabbit, or -human IgG conjugated with HRP (Jackson ImmunoResearch, Cambridgeshire, UK) as visualized using the SuperSignal chemiluminescence detection system (Pierce, Rockford, Ill.).

Figure 4:
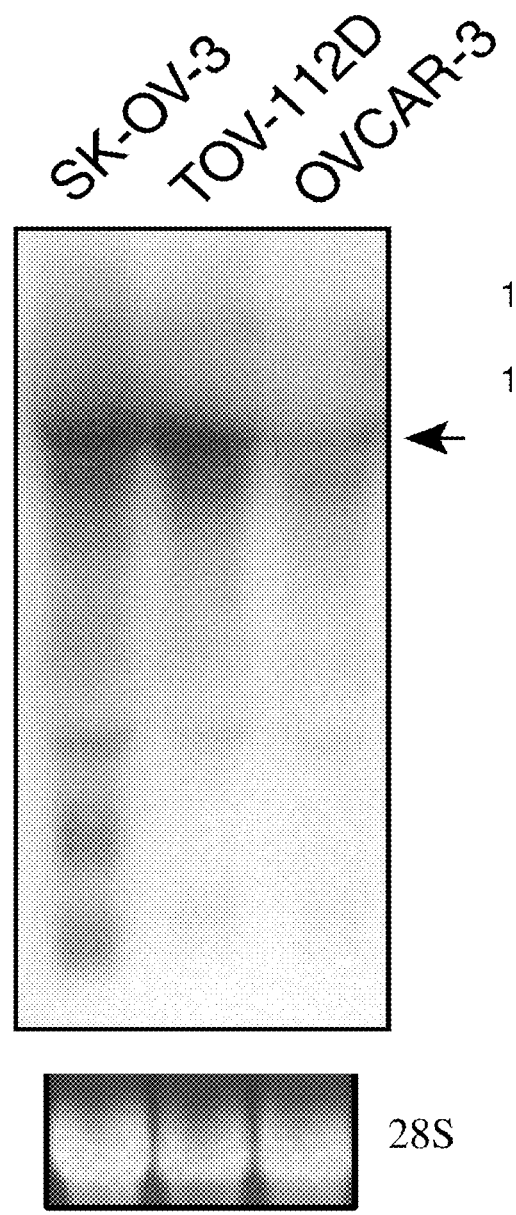
FIG. 4 shows the determination of sizes of OVTA1 gene transcript in ovarian cancer cells. Determination of sizes of OVTA1 gene transcript(s) was carried out by Northern analyses of ovarian cancer cells. The total RNAs extracted from SK-OV-3, OVCAR3, and TOV-112D cells were resolved on a denaturing formaldehyde-containing gel. An antisense sequence specifically primed on OVTA1 gene transcript was radiolabelled with [α-32 P]dATP and hybridized with the extracted RNA of those cells.
Figure 5:
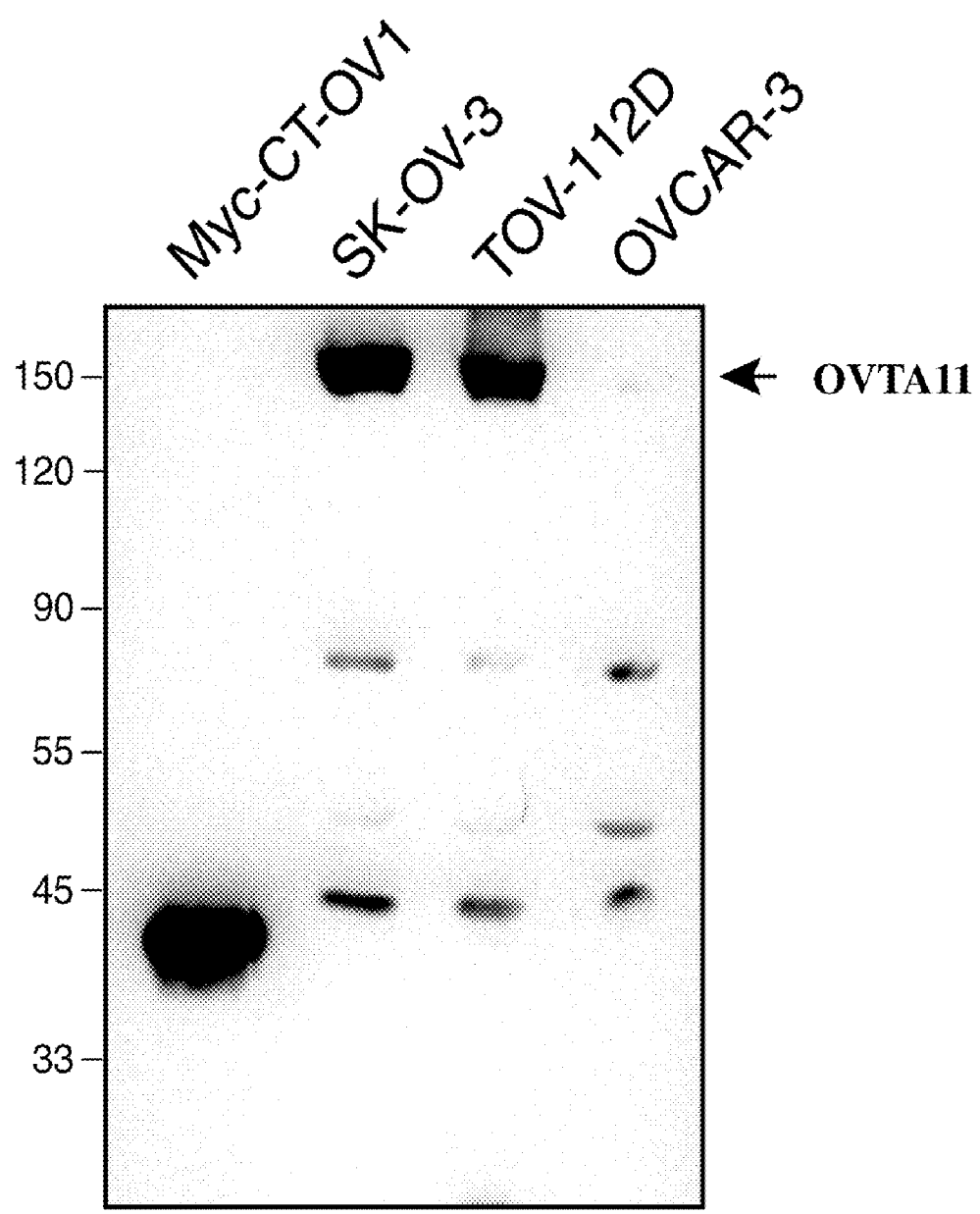
FIG. 5 shows that the putative KIAA0999 gene published in NCBI database could be translated into a 150 KDa-polypeptide chain. In Western blotting analyses using a rabbit antiserum made from the C-terminus of OVTA1, ovarian cancer cells consistently showed four protein bands (FIG. 5). A major protein around 150 KDa is found in all the cells, suggesting that the coding sequence of OVTA1 gene is approximately 4.0 Kb.

Characterization of OVTA1 transcript and protein in ovarian cancer cells. To determine the actual sizes of naturally occurring transcript and its encoded polypeptide of OVTA1 in ovarian cells, Northern and Western blotting analyses were carried out. Using an antisense probe embracing the sequence coding for the 7-mer peptide, Northern blotting analysis clearly indicated a ~4.5 kb band as the major corresponding transcript for OVTA1 gene in SK-OV3 and TOV-112D cells while showing a significantly low level of the transcript in OVCAR3 cells (FIG. 4). Simultaneously, a recombinant CT-OVTA1 gene was constructed that was fused with GST tag sequence, and the recombinant antigen was expressed and purified for generation of OVTA1-specific rabbit antiserum. The specificity of the antiserum has been confirmed by Western blotting analysis of HeLa cells expressing either myc-tagged CT-OVTA1 gene or vector control (data not shown). Consistently, the molecular weight of a major immuno-reactive protein is around 150 KDa in SK-OV3 and TOV-112D cells, but rarely detected in OVCAR3 cells (FIG. 5). The experiment using an in vitro transcript and translation couple system demonstrated that the putative KIAA0999 gene (i.e., OVTA1 gene in this invention) published in NCBI database (Access number: AB023216) could be translated into a 150 KDa-polypeptide chain (FIG. 5) and be immunoreactive to OVTA1 antiserum (data not shown). Thus, taken together, these data clearly indicate that OVTA1 gene is a functional allele and encode a 150 KDa protein in ovarian cancer cells.

Figure 6:
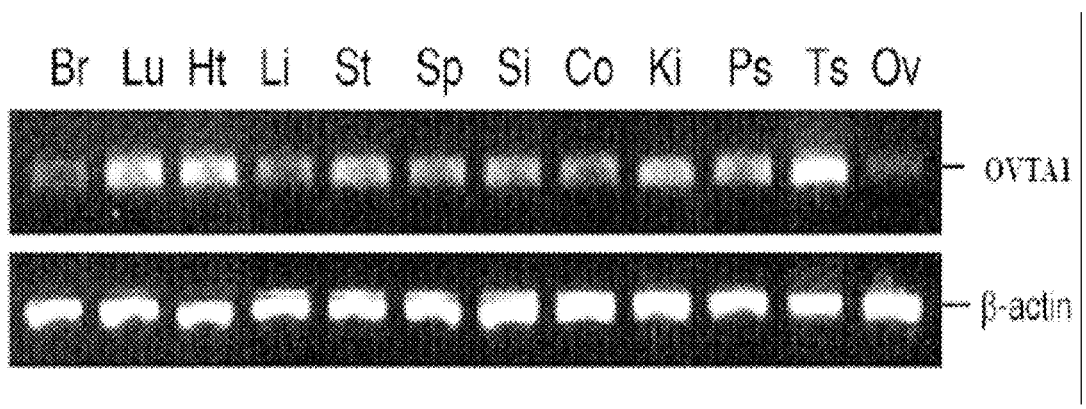
FIG. 6 shows that OVTA 1 universally existed in multiple tissues.

Tissue distribution of OVTA1 expression. To determine OVTA1 gene expression in a variety of tissues, we performed polymerase chain reaction (PCR) of cDNA libraries from 12 normal human tissues using two pairs of gene-specific primer located in the 3'-coding and -untranslated regions of OVTA1 gene. Nested PCR analyses shown in FIG. 6 indicated that OVTA1 universally existed in multiple tissues with a distinct difference in its expression level. Relatively higher levels of its expression are observed in the lungs, heart, and testes, whereas significantly low levels are observed in the brain and ovaries.

Example 3

Increase in Cell Proliferation Rate and Cell Migration by Over-Expression of OVTA1

Over-expression of OVTA1 in OVCAR3 cells Establishment of OVCAR3 Stable Clones: OVTA1 gene was constructed from SK-OV3 ovarian cancer cells by using RT-PCR (sense, 5'-CGG GAA TTC TCT CAG CAA CAT GCC AGG C-3' (SEQ ID NO:23); antisense, 5'-AAT GAA TTC TCA GTT GAT TAG GGC AGA-3' (SEQ ID NO:24)). The pcDNA-OVTA1 plasmid was constructed by using the following specific primers: 5'-CGC CAG TGT GCT GGA ATT CTG CTG TCC GGC GCG AGC-3' (SEQ ID NO:25); antisense, 5'-GCA TGC TCG AGC GGC CGC TTA CAC GCC TGC CTG CTC CAT-3' (SEQ ID NO:26). OVCAR3 cells were transfected with 1 µg of pcDNA-OVTA1 plasmid for the establishment of OVTA1 stable clones or with pcDNA3.1 for the vector controls. The stable clones were selected from the medium containing 400 µg/ml of G418 after 4 weeks. The expression levels were confirmed by RT-PCR and Western blot analysis.

Figure 7:
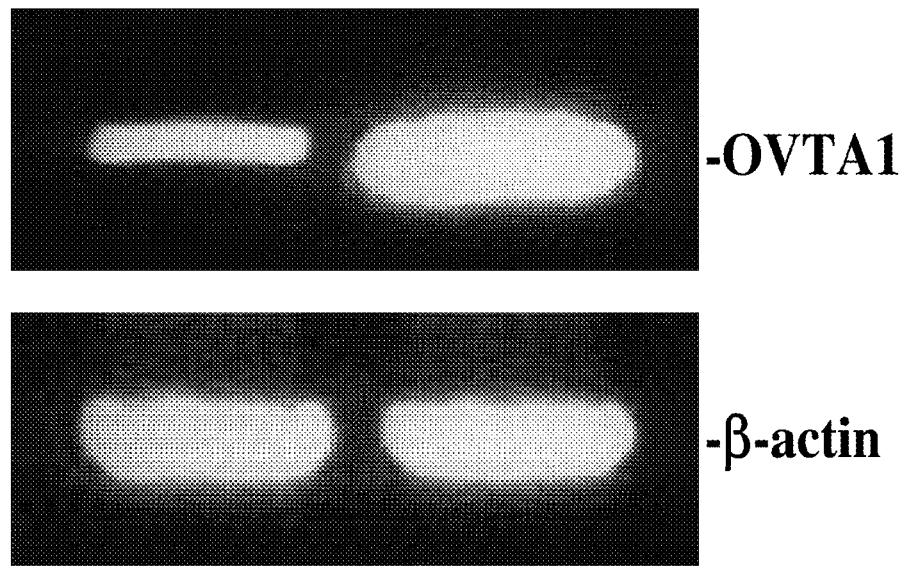
FIG. 7 shows the over-expression of OVTA1 in OVCAR-3 cells.
Figure 7:
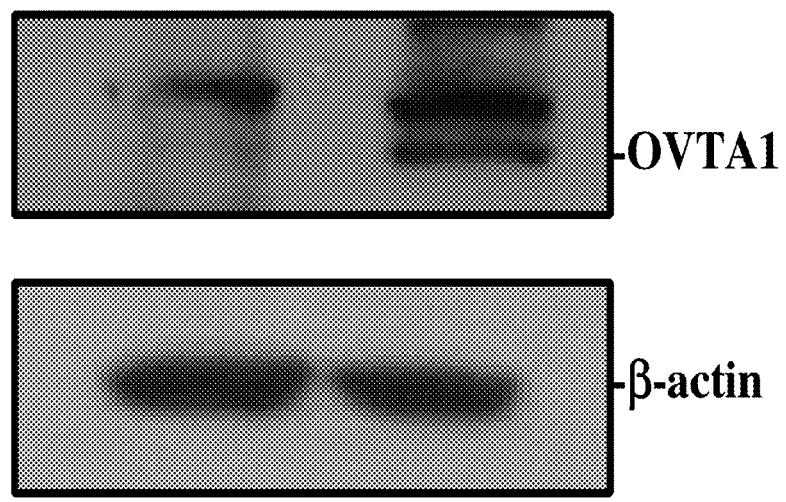

Expression of OVTA1 leads to cell proliferation and migration in ovarian cancer cells It is known that SK-OV3 shows a higher cell proliferation rate in vitro compared to OVCAR3 cells. To investigate whether OVTA1 antigen was associated with ovarian tumorogenesis, SK-OV3 cells were either transfected with pLKO.1-shOVTA1 or with pLKO.1 vector as a mock control. Meanwhile, OVCAR3 cells were transfected with pcDNA or pcDNA-OVTA1 vector. RT-PCR and Western blot were performed to show that both OVTA1 mRNA and protein levels increased in pcDNA-OVTA1 transfected OVCAR3 cells (FIG. 7).

Migration assay. The cell migration experiments were performed using in vitro transwell assays. $5 \times 10^4$ cells were resuspended in serum-free medium and seeded in a culture insert containing membrane with 8 µm pore size (Costar, Cambridge, Mass., USA). After placing the insert onto a well pre-filled with M199 medium plus 10% FBS, the cells were cultured at 37° C. for 6 hours. The number of the cells migrating from the upper chamber into the bottom side of the insert by chemo-attraction was counted as described by manufacturer's instruction (Costar).

Figure 8A:
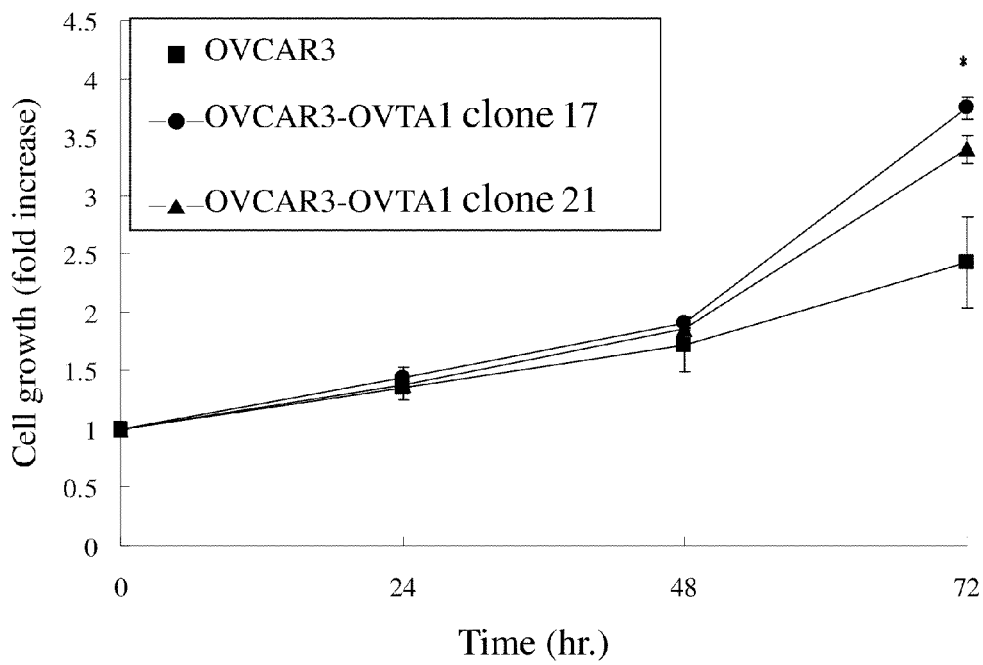
FIGS. 8A and 8B show that the over-expression of OVTA1 in OVCAR3 cells significantly increased cell proliferation rate and cell migration (metastasis) by around 2.75 to 3.1 times, respectively, compared to control (FIG. 8B).
Figure 8B:
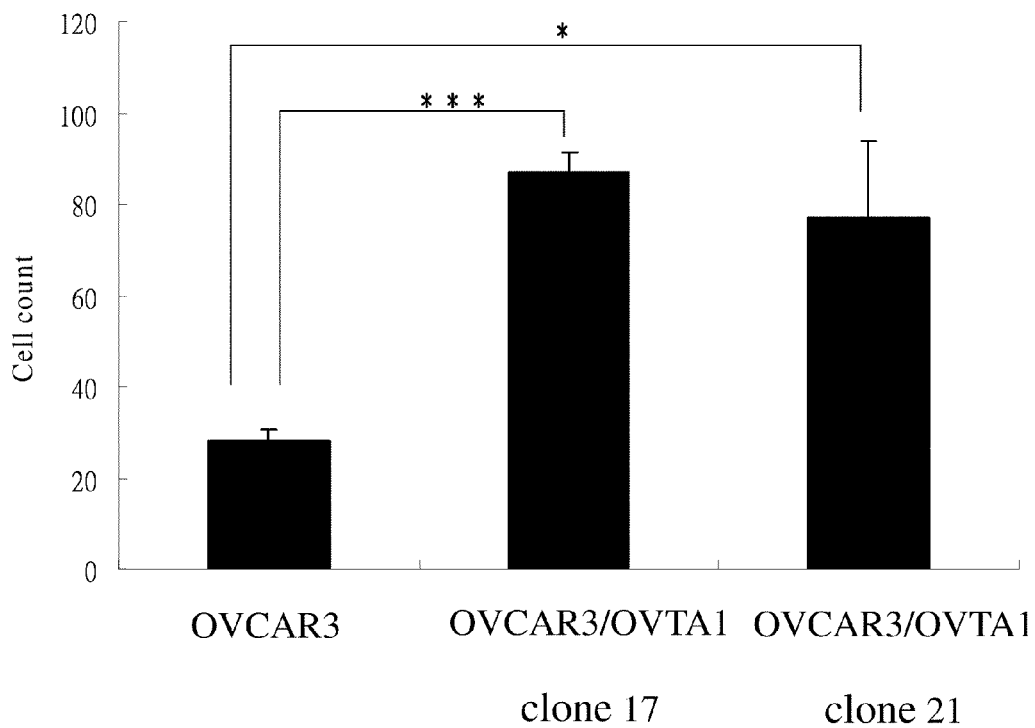

Consequently, the over-expression of OVTA1 in OVCAR3 cells significantly increased cell proliferation rate (FIG. 8A) and cell migration (metastasis) (FIG. 8B) by around 2.75 to 3.1 times compared to control.

Example 4

Knockdown of OVTA1

Figure 9:
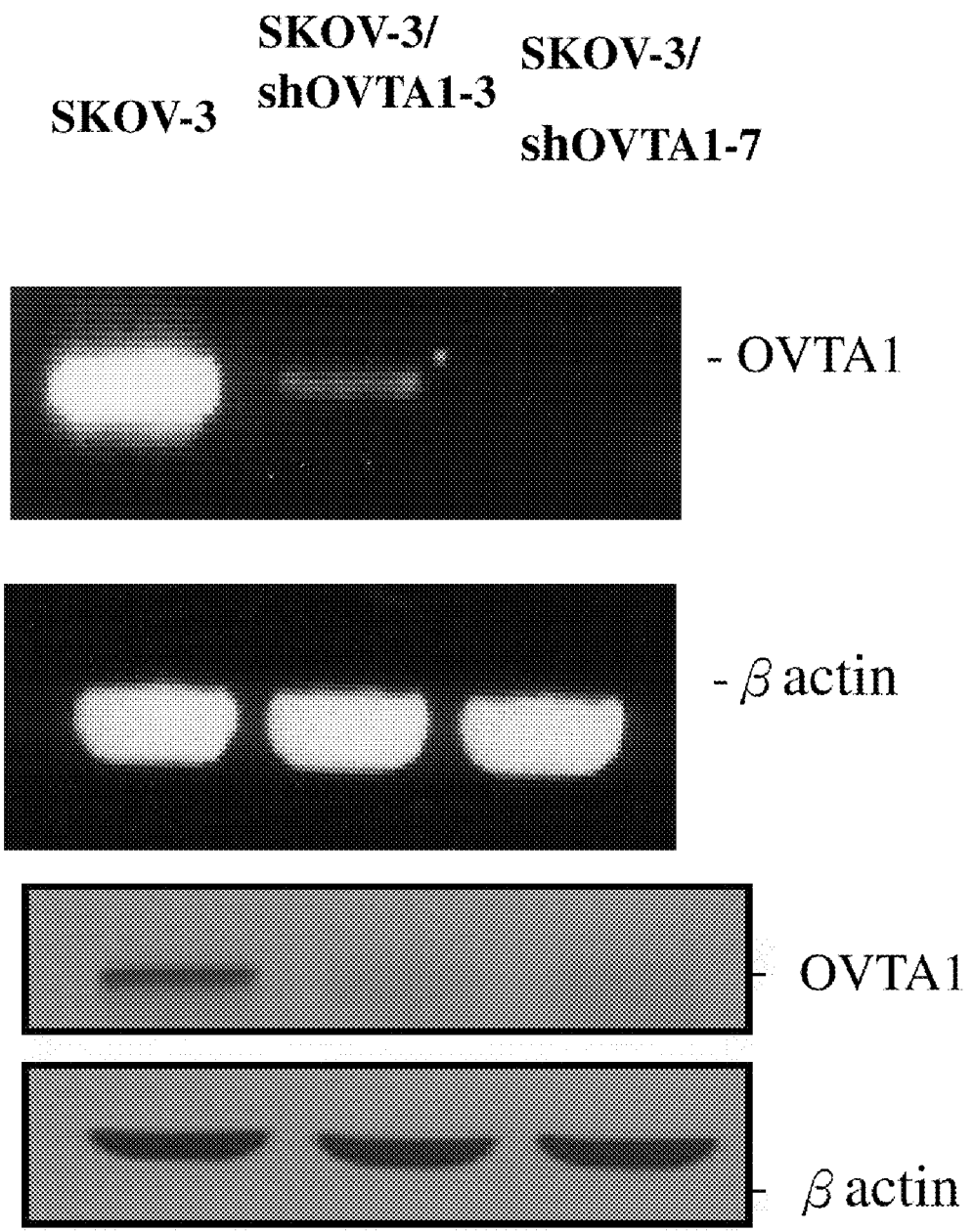
FIG. 9 shows the knockdown of OVTA1 in SKOV-3 cells.
Figure 10A:
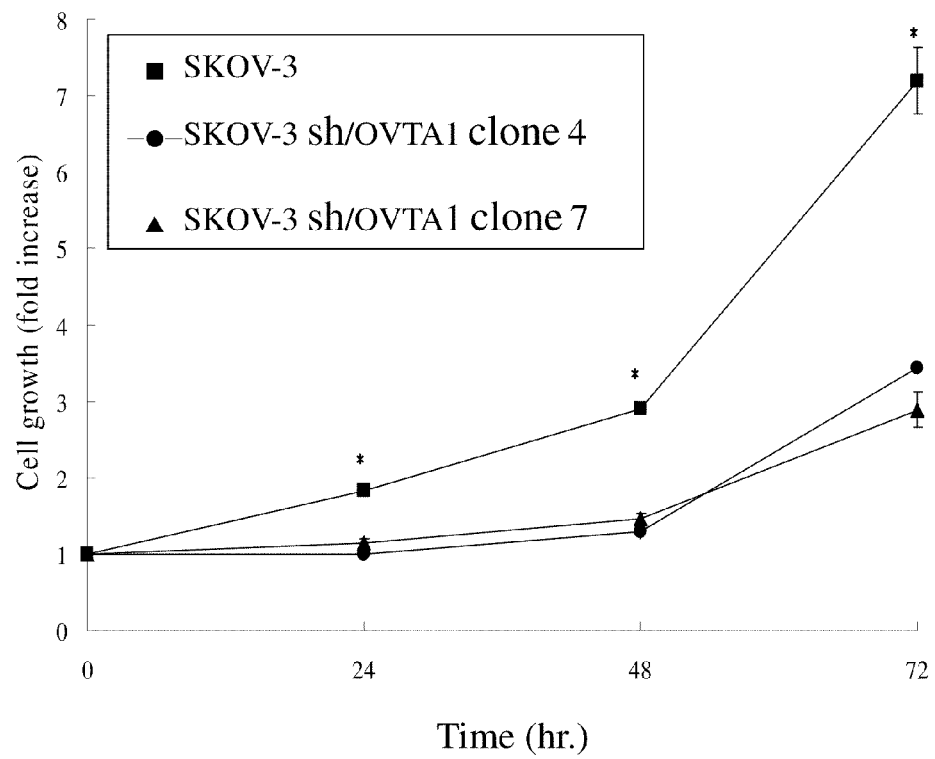
FIGS. 10A and 10B show that the suppression of OVTA1 expression in SK-OV3 cells significantly inhibited cell proliferation rate and cell migration (metastasis), respectively.
Figure 10B:
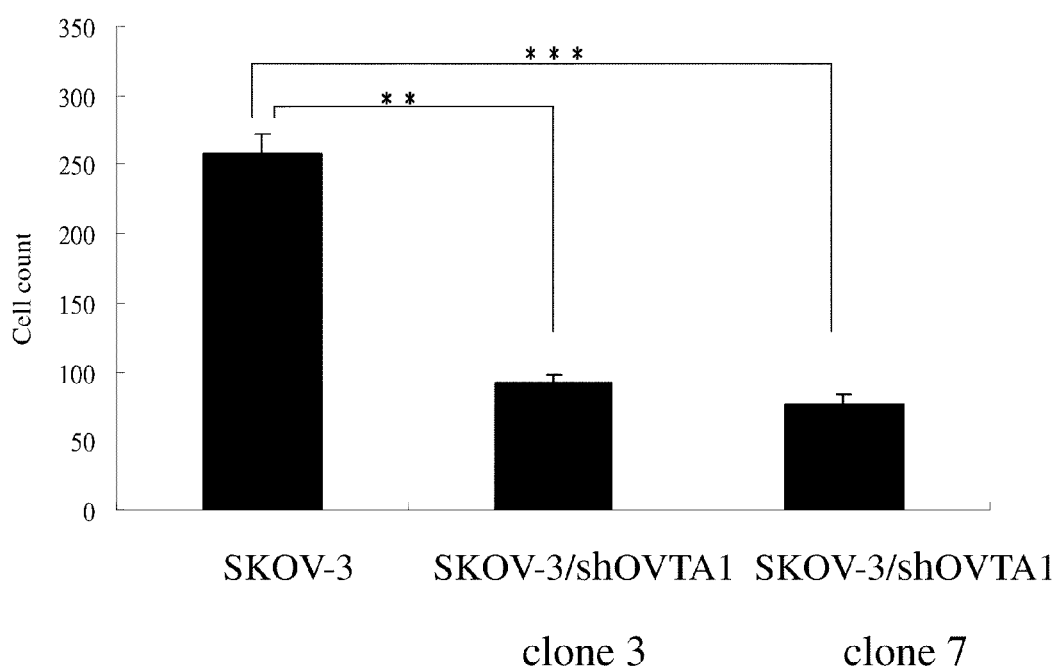

Knockdown of OVTA1 by small interfering RNA in SK-OV3 cells. The pLKO.1-shOVTA1 vector containing 5'-CCGGGCCAGGCTTTATCTTATCAAACTC-GAGTTTGATAAGATAAAGCCTGGCTTTTTG (SEQ ID NO:27) and pLKO.1 control vector (Open Biosystems) were prepared. SK-OV3 cells were transfected with 1 µg of pLKO.1-shOVTA1 or pLKO.1 as control. The stable clones were selected by 2.5 µg/ml of puromycin for 4 weeks and the efficiency of interference was analyzed using RT-PCR and Western blotting. The RT-PCR and Western blot analysis showed that OVTA1 mRNA and protein expressions were suppressed in SK-OV3 cells transfected with pLKO.1-shOVTA1 in the knockdown experiments (FIG. 9). As a result, the suppression of OVTA1 expression in SK-OV3 cells significantly inhibited cell proliferation rate (FIG. 10A) and cell migration (metastasis) (FIG. 10B). Taken together, these data suggest that high levels of OVTA1 may promote tumor cell proliferation and metastasis in human ovarian cancer cells.

Example 5

Correlation Between OVTA1 Expression and Tumor Progression

Xenograft Mouse Models of Ovarian Cancer. Five- to six-week-old SCID mice were purchased from the Animal Center of Tzu Chi University, Hualien, Taiwan. Animals were maintained under specific pathogen-free conditions and provided with sterile food and water. The mice were allowed to acclimatize for at least six days. SK-OV3 and transfectants with pLKO.1-shOVTA1 or vector control were subcutaneously injected into the mice ($1 \times 10^6$ cells per mouse in 0.1 ml of phosphate buffered saline under aseptic conditions). Tumor sizes were observed and recorded weekly by measuring tumor length (L) and width (W) using a caliper. Tumor volume was calculated from measurements of width and length as: tumor volume (width/2)2×length×π (reference).

Figure 11A:
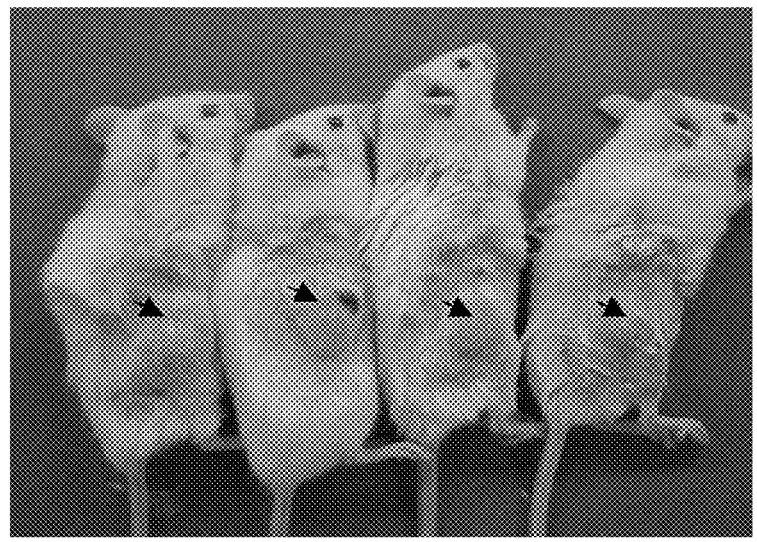
FIG. 11A shows that tumors developed in all the mice subcutaneously inoculated with SK-OV3 cells but not in the mice inoculated with SK-OV3/shOVTA1 cells.
Figure 11A:
Figure 11B:
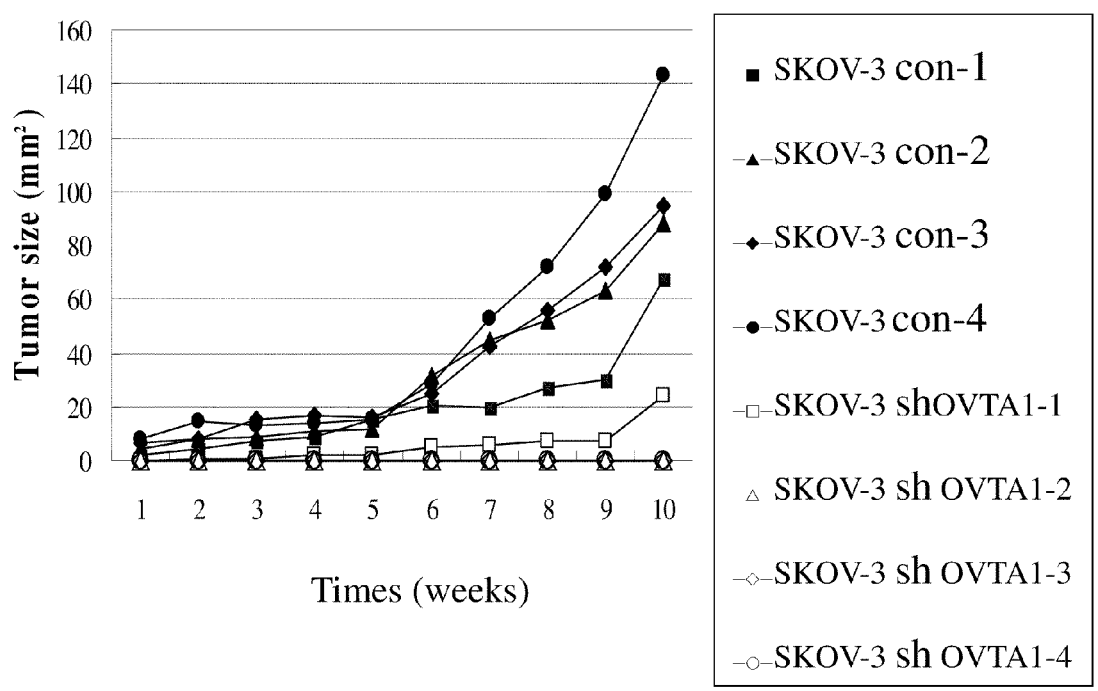
FIG. 11B shows that the knockdown of OVTA1 decreases tumor growth rate in NOD-SCID mice.

OVTA1 expression is correlated with tumor progression. To further investigate the role of OVTA1 in vivo, SCID mice were subcutaneously injected with SK-OV3 cells transfected with pLKO.1-shOVTA1 or control vector. The tumor growth in each mouse was monitored weekly. The tumor sizes were measured for a total of 8 weeks after cell inoculation. Tumors developed in all the mice subcutaneously inoculated with SK-OV3 cells but not in the mice inoculated with SK-OV3/shOVTA1 cells (FIG. 11A). The knockdown of OVTA1 decreases tumor growth rate in NOD-SCID mice (FIG. 11B).

These observations strongly suggest that the OVTA1 plays a critical role in tumor progression.

Example 5

Use of the Antigen Polypeptide of the Invention as Target of Diagnosis of Ovarian Cancer Immunohistochemistry. Formalin-fixed, paraffin-embedded tissue samples were obtained from cooperating hospitals and stained with anti-GST control antibody or antibody specific to CA125 (Dako, Carpinteria, Calif.) or OVTA1 using a conventional method. The sections were serially dewaxed, re-hydrated, and washed with PBS. After 20 min heat-mediated antigen retrieval process in 10 mM sodium citrate (pH 6.0), the sections were rinsed with a wash buffer [10 mM Tris-HCl (pH 7.4) and 150 mM sodium chloride] three times followed by treatment with 3% hydrogen peroxide for 5 min to block endogenous peroxidases. After PBS wash, the samples were incubated with the diluted primary antibody (1:20 for CA125, 1:4000 for OVTA1 rabbit antiserum, or 1:2000 dilution for home-made rabbit anti-GST antiserum) for 1 hour at room temperature or overnight at 4° C. The primary antibodies were detected using LSAB kit (Dako) and the slides were counter-stained with hematoxylin. The expression statuses of OVTA1 and CA125 were accessed and graded at a final magnification of 200× independently by two pathologists in a blinded manner. Conflicting scores were resolved with a discussion microscope.

Figure 12:
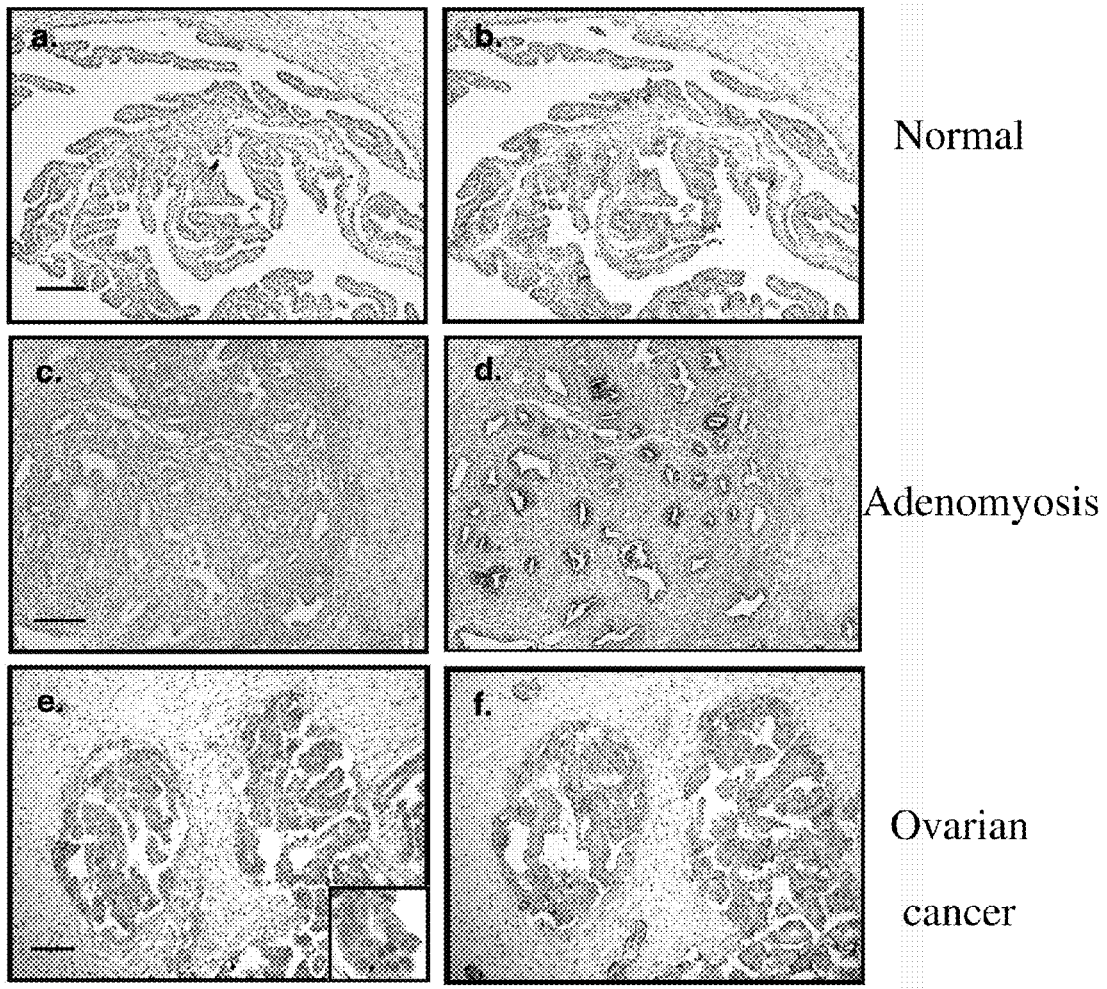
FIG. 12 shows the immunohistochemic results that clearly demonstrate that OVTA1 is over-expressed in ovarian cancer tissues (e) compared to normal ovarian tissues (a) or tissues from adenomyosis (c). In contrast, CA-125 antigen can be detected in both ovarian cancer tissues (f) and tissues from adenomyosis (d). In (b), the normal ovarian tissue as the control for CA-125 antigen detection is shown.

OVTA1 over-expression in ovarian cancer tissues. 40 tissue sections from non-cancer ovary and 39 from ovarian cancer tissues were prepared and examined for their OVTA1 and CA125 expression using either anti-OVTA1 or conventional anti-CA125 antibodies. The immunohistochemic results clearly show that OVTA1 is over-expressed in ovarian cancer tissues compared to normal ovarian tissues or tissues from adenomyosis. In contrast, CA-125 antigen can be detected in both ovarian cancer tissues and tissues from adenomyosis. A representative result is shown in FIG. 12. The statistical results are summarized in Table 2 below, and indicate that OVTA1 antigen was exclusively detected in ovarian cancer but not in non-cancer tissues. In sum, it is suggested that OVTA1 antigen is a better diagnostic target than CA125, which is routinely used for the detection of ovarian cancer.

TABLE 2

| | Subtype | Total | Metastasis | | CA-125 | | | OVTA-1 | |
| --- | --- | --- | --- | --- | --- | --- | --- | --- | --- |
| | | | | | Positive | Negative | Trace | Positive | Negative | Trace |
| Non-ovarian cancer | Normal ovary | 20 | | | 2 | 16 | 2 | 1 | 19 | 0 |
| | Adenomyosis | 10 | | | 7 | 2 | 1 | 0 | 10 | 0 |
| | Leiomyoma | 10 | | | 2 | 8 | 0 | 0 | 10 | 0 |
| | Total | 40 | | | 11 (27.5%) | 26 (65%) | 3 | 1 (2.5%) | 39 (97.5%) | 0 |
| Ovarian cancer | Serous | 13 | Yes | 12 | 12 | 0 | 0 | 9 | 1 | 2 |
| | | | No | 1 | 0 | 1 | 0 | 0 | 1 | 0 |
| | Endometriod | 8 | Yes | 5 | 5 | 0 | 0 | 3 | 2 | 0 |
| | | | No | 3 | 3 | 0 | 0 | 0 | 3 | 0 |
| | Clear cell | 6 | Yes | 1 | 1 | 0 | 0 | 1 | 0 | 0 |
| | | | No | 5 | 3 | 2 | 0 | 2 | 3 | 0 |
| | Mucinous | 3 | Yes | 1 | 1 | 0 | 0 | 0 | 1 | 0 |
| | | | No | 2 | 0 | 2 | 0 | 0 | 2 | 0 |
| | Yolk sac | 1 | Yes | 1 | 0 | 1 | 0 | 0 | 1 | 0 |
| | | | No | 0 | 0 | 0 | 0 | 0 | 0 | 0 |
| | Mixed | 2 | Yes | 2 | 2 | 0 | 0 | 0 | 2 | 0 |
| | | | No | 0 | 0 | 0 | 0 | 0 | 0 | 0 |
| | Others | 6 | Yes | 6 | 4 | 2 | 0 | 3 | 2 | 1 |
| | | | No | 0 | 0 | 0 | 0 | 0 | 0 | 0 |
| | Total | | Yes | 28 | 25 | 3 | 0 | 16 | 9 | 3 |
| | | | No | 11 | 6 | 5 | 0 | 2 | 9 | 0 |

What is claimed is:

1. An isolated antigen polypeptide expressed in a subject with ovarian cancer, selected from the group consisting of: (a) a first polypeptide consisting of a first amino acid sequence consisting of at least 85% sequence identity with SEQ ID NO:2; (b) a second polypeptide encoded by a first polynucleotide consisting of a nucleotide sequence consisting of at least 85% sequence identity with SEQ ID NO: 1; and (c) a third polypeptide consisting of a first amino acid fragment encoded by a second polynucleotide as shown in SEQ ID NO: 4 or consisting of a second amino acid fragment as shown in SEQ ID NO: 3, provided that the sequence of the third polypeptide is included within (a) or (b).

2. The isolated antigen polypeptide of claim 1, wherein the sequence identity in (a) and (b) is at least 90%, 95% or 98%.

3. The isolated antigen polypeptide of claim 1, which is encoded by a polynucleotide consisting a nucleotide sequence as shown in SEQ ID NO: 1 or SEQ ID NO: 4.

4. The isolated antigen polypeptide of claim 1, which consists the first amino acid sequence as shown in SEQ ID NO:2 or the second amino acid fragment of SEQ ID NO:3.

5. A kit for the detection of ovarian cancer in a subject comprising the antigen polypeptide as claimed in claim 1.

* * * * *

SEQUENCE LISTING

<160> NUMBER OF SEQ ID NOS: 27

<210> SEQ ID NO 1
<211> LENGTH: 3792
<212> TYPE: DNA
<213> ORGANISM: Homo sapiens

<400> SEQUENCE: 1

```
atgcccgccc gtatcggcta ctacgagatc gaccgcacca tcggcaaggg caacttcgcg      60
gtggtcaagc gggccacgca cctcgtcacc aaggccaagg ttgctatcaa gatcatagat     120
aagacccagc tggatgaaga aaacttgaag aagatttttcc gggaagttca aattatgaag     180
atgctttgcc acccccatat catcaggctc taccaggtta tggagacaga acggatgatt     240
```

| | |
|---|---|
| tatctggtga cagaatatgc tagtggaggg gaaatatttg accacctggt ggcccatggt | 300 |
| agaatggcag aaaaggaggc acgtcggaag ttcaaacaga tcgtcacagc tgtctatttt | 360 |
| tgtcactgtc ggaacattgt tcatcgtgat ttaaaagctg aaaatttact tctggatgcc | 420 |
| aatctgaata tcaaaatagc agattttggt ttcagtaacc tcttcactcc tgggcagctg | 480 |
| ctgaagacct ggtgtggcag ccctccctat gctgcacctg aactctttga aggaaaagaa | 540 |
| tatgatgggc ccaaagtgga catctggagc cttggagttg tcctctacgt gcttgtgtgc | 600 |
| ggtgccctgc catttgatgg aagcacactg cagaatctgc gggcccgcgt gctgagtgga | 660 |
| aagttccgca tcccattttt tatgtccaca gaatgtgagc atttgatccg ccatatgttg | 720 |
| gtgttagatc ccaataagcg cctctccatg gagcagatct gcaagcacaa gtggatgaag | 780 |
| ctaggggacg ccgatcccaa ctttgacagg ttaatagctg aatgccaaca actaaaggaa | 840 |
| gaaagacagg tggaccccct gaatgaggat gtcctcttgg ccatggagga catgggactg | 900 |
| gacaaagaac agacactgca gtcattaaga tcagatgcct atgatcacta tagtgcaatc | 960 |
| tacagcctgc tgtgtgatcg acataagaga cataaaaccc tgcgtctcgg agcacttcct | 1020 |
| agcatgcccc gagccctggc cttcaagca ccagtcaata tccaggcgga gcaggcaggt | 1080 |
| actgctatga acatcagcgt tccccaggtg cagctgatca acccagagaa ccaaattgtg | 1140 |
| gagccggatg ggacactgaa tttgacagt gatgaggtg aagagccttc ccctgaagca | 1200 |
| ttggtgcgct atttgtcaat gaggaggcac acagtgggtg tggctgaccc acgcacggaa | 1260 |
| gttatgaag atctgcagaa gctcctacct ggctttcctg gagtcaaccc ccaggctcca | 1320 |
| ttcctgcagg tggcccctaa tgtgaacttc atgcacaacc tgttgcctat gcaaaacttg | 1380 |
| caaccaaccg ggcaacttga gtacaaggag cagtctctcc tacagccgcc cacgctacag | 1440 |
| ctgttgaatg gaatgggccc ccttggccgg agggcatcag atggaggagc caacatccaa | 1500 |
| ctgcatgccc agcagctgct gaagcgccca cggggaccct ctccgcttgt caccatgaca | 1560 |
| ccagcagtgc cagcagttac ccctgtggac gaggagagct cagacgggga gccagaccag | 1620 |
| gaagctgtgc agagctctac ctacaaggac tccaacactc tgcacctccc tacggagcgt | 1680 |
| ttctccctg tgcgccggtt ctcagatggg gctgcgagca tccaggcctt caaagctcac | 1740 |
| ctggaaaaaa tgggcaacaa cagcagcatc aaacagctgc agcaggagtg tgagcagctg | 1800 |
| cagaagatgt acgggggca gattgatgaa agaaccctgg agaagaccca gcagcagcat | 1860 |
| atgttatacc agcaggagca gcaccatcaa attctccagc aacaaattca agactctatc | 1920 |
| tgtcctcctc agccatctcc acctcttcag gctgcatgtg aaaatcagcc agccctcctt | 1980 |
| acccatcagc tccagaggtt aaggattcag ccttcaagcc cacccccaa ccaccccaac | 2040 |
| aaccatctct tcaggcagcc cagtaatagt cctccccca tgagcagtgc catgatccag | 2100 |
| cctcacgggg ctgcatcttc ttcccagttt caaggcttac cttcccgcag tgcaatcttt | 2160 |
| cagcagcaac tgagaactg ttcctctcct cccaacgtgg cactaacctg cttgggtatg | 2220 |
| cagcagcctg ctcagtcaca gcaggtcacc atccaagtcc aagagcctgt tgacatgctc | 2280 |
| agcaacatgc caggcacagc tgcaggctcc agtgggcgcg gcatctccat cagccccagt | 2340 |
| gctggtcaga tgcagatgca gcaccgtacc aacctgatgg ccaccctcag ctatgggcac | 2400 |
| cgtcccttgt ccaagcagct gagtgctgac agtcagagg ctcacagctt gaacgtgaat | 2460 |
| cggttctccc ctgctaacta cgaccaggcg catttacacc cccatctgtt ttcggaccag | 2520 |
| tcccggggtt cccccagcag ctacagccct caacaggag tggggttctc tccaacccaa | 2580 |
| gccctgaaag tccctccact tgaccaattc cccaccttcc ctcccagtgc acatcagcag | 2640 |

```
ccgccacact ataccacgtc ggcactacag caggccctgc tgtctcccac gccgccagac    2700
tatacaagac accagcaggt accccacatc cttcaaggac tgctttctcc ccggcattcg    2760
ctcaccggcc actcggacat ccggctgccc ccaacagagt ttgcacagct cattaaaagg    2820
cagcagcaac aacggcagca gcagcagcaa cagcagcaac agcaagaata ccaggaactg    2880
ttcaggcaca tgaaccaagg ggatgcgggg agtctggctc ccagccttgg gggacagagc    2940
atgacagagc gccaggcttt atcttatcaa aatgctgact cttatcacca tcacaccagc    3000
ccccagcatc tgctacaaat cagggcacaa gaatgtgtct cacaggcttc ctcacccacc    3060 ccgcccacg ggtatgctca ccagccggca ctgatgcatt cagagagcat ggaggaggac    3120
tgctcgtgtg agggggccaa ggatggcttc aagacagta agagttcaag tacattgacc    3180
aaaggttgcc atgacagccc tctgctcttg agtaccggtg gacctgggga ccctgaatct    3240
ttgctaggaa ctgtgagtca tgcccaagaa ttggggatac atccctatgg tcatcagcca    3300
actgctgcat tcagtaaaaa taaggtgccc agcagagagc ctgtcatagg gaactgcatg    3360
gatagaagtt ctccaggaca agcagtggag ctgccggatc acaatgggct cgggtaccca    3420
gcacgcccct ccgtccatga gcaccacagg ccccgggccc tccagagaca ccacacgatc    3480
cagaacagcg acgatgctta tgtacagctg gataacttgc aggaatgag tctcgtggct    3540 gggaaagcac ttagctctgc ccggatgtcg gatgcagttc tcagtcagtc ttcgctcatg    3600
ggcagccagc agtttcagga tggggaaaat gaggaatgtg gggcaagcct gggaggtcat    3660
gagcacccag acctgagtga tggcagccag catttaaact cctcttgcta tccatctacg    3720
tgtattacag acattctgct cagctacaag caccccgaag tctccttcag catggagcag    3780
gcaggcgtgt aa                                                       3792
```

<210> SEQ ID NO 2
<211> LENGTH: 1263
<212> TYPE: PRT
<213> ORGANISM: Homo sapiens

<400> SEQUENCE: 2

```
Met Pro Ala Arg Ile Gly Tyr Tyr Glu Ile Asp Arg Thr Ile Gly Lys
1               5                   10                  15

Gly Asn Phe Ala Val Val Lys Arg Ala Thr His Leu Val Thr Lys Ala
            20                  25                  30

Lys Val Ala Ile Lys Ile Ile Asp Lys Thr Gln Leu Asp Glu Glu Asn
        35                  40                  45

Leu Lys Lys Ile Phe Arg Glu Val Gln Ile Met Lys Met Leu Cys His
    50                  55                  60

Pro His Ile Ile Arg Leu Tyr Gln Val Met Glu Thr Glu Arg Met Ile
65                  70                  75                  80

Tyr Leu Val Thr Glu Tyr Ala Ser Gly Gly Glu Ile Phe Asp His Leu
                85                  90                  95

Val Ala His Gly Arg Met Ala Glu Lys Glu Ala Arg Arg Lys Phe Lys
            100                 105                 110

Gln Ile Val Thr Ala Val Tyr Phe Cys His Cys Arg Asn Ile Val His
        115                 120                 125

Arg Asp Leu Lys Ala Glu Asn Leu Leu Leu Asp Ala Asn Leu Asn Ile
    130                 135                 140

Lys Ile Ala Asp Phe Gly Phe Ser Asn Leu Phe Thr Pro Gly Gln Leu
145                 150                 155                 160

Leu Lys Thr Trp Cys Gly Ser Pro Pro Tyr Ala Ala Pro Glu Leu Phe
                165                 170                 175
```

-continued

Glu Gly Lys Glu Tyr Asp Gly Pro Lys Val Asp Ile Trp Ser Leu Gly
            180                 185                 190

Val Val Leu Tyr Val Leu Val Cys Gly Ala Leu Pro Phe Asp Gly Ser
            195                 200                 205

Thr Leu Gln Asn Leu Arg Ala Arg Val Leu Ser Gly Lys Phe Arg Ile
            210                 215                 220

Pro Phe Phe Met Ser Thr Glu Cys Glu His Leu Ile Arg His Met Leu
225                 230                 235                 240

Val Leu Asp Pro Asn Lys Arg Leu Ser Met Glu Gln Ile Cys Lys His
                245                 250                 255

Lys Trp Met Lys Leu Gly Asp Ala Asp Pro Asn Phe Asp Arg Leu Ile
                260                 265                 270

Ala Glu Cys Gln Gln Leu Lys Glu Glu Arg Gln Val Asp Pro Leu Asn
            275                 280                 285

Glu Asp Val Leu Leu Ala Met Glu Asp Met Gly Leu Asp Lys Glu Gln
290                 295                 300

Thr Leu Gln Ser Leu Arg Ser Asp Ala Tyr Asp His Tyr Ser Ala Ile
305                 310                 315                 320

Tyr Ser Leu Leu Cys Asp Arg His Lys Arg His Lys Thr Leu Arg Leu
                325                 330                 335

Gly Ala Leu Pro Ser Met Pro Arg Ala Leu Ala Phe Gln Ala Pro Val
            340                 345                 350

Asn Ile Gln Ala Glu Gln Ala Gly Thr Ala Met Asn Ile Ser Val Pro
            355                 360                 365

Gln Val Gln Leu Ile Asn Pro Glu Asn Gln Ile Val Glu Pro Asp Gly
            370                 375                 380

Thr Leu Asn Leu Asp Ser Asp Glu Gly Glu Pro Ser Pro Glu Ala
385                 390                 395                 400

Leu Val Arg Tyr Leu Ser Met Arg Arg His Thr Val Gly Val Ala Asp
                405                 410                 415

Pro Arg Thr Glu Val Met Glu Asp Leu Gln Lys Leu Leu Pro Gly Phe
            420                 425                 430

Pro Gly Val Asn Pro Gln Ala Pro Phe Leu Gln Val Ala Pro Asn Val
            435                 440                 445

Asn Phe Met His Asn Leu Leu Pro Met Gln Asn Leu Gln Pro Thr Gly
            450                 455                 460

Gln Leu Glu Tyr Lys Glu Gln Ser Leu Leu Gln Pro Pro Thr Leu Gln
465                 470                 475                 480

Leu Leu Asn Gly Met Gly Pro Leu Gly Arg Arg Ala Ser Asp Gly Gly
                485                 490                 495

Ala Asn Ile Gln Leu His Ala Gln Gln Leu Leu Lys Arg Pro Arg Gly
            500                 505                 510

Pro Ser Pro Leu Val Thr Met Thr Pro Ala Val Pro Ala Val Thr Pro
            515                 520                 525

Val Asp Glu Glu Ser Ser Asp Gly Glu Pro Asp Gln Glu Ala Val Gln
530                 535                 540

Ser Ser Thr Tyr Lys Asp Ser Asn Thr Leu His Leu Pro Thr Glu Arg
545                 550                 555                 560

Phe Ser Pro Val Arg Arg Phe Ser Asp Gly Ala Ala Ser Ile Gln Ala
                565                 570                 575

Phe Lys Ala His Leu Glu Lys Met Gly Asn Asn Ser Ser Ile Lys Gln
            580                 585                 590

Leu Gln Gln Glu Cys Glu Gln Leu Gln Lys Met Tyr Gly Gly Gln Ile

```
                595                 600                 605
Asp Glu Arg Thr Leu Glu Lys Thr Gln Gln His Met Leu Tyr Gln
        610                 615                 620
Gln Glu Gln His His Gln Ile Leu Gln Gln Ile Gln Asp Ser Ile
625                 630                 635                 640
Cys Pro Pro Gln Pro Ser Pro Leu Gln Ala Ala Cys Glu Asn Gln
                645                 650                 655
Pro Ala Leu Leu Thr His Gln Leu Gln Arg Leu Arg Ile Gln Pro Ser
                660                 665                 670
Ser Pro Pro Asn His Pro Asn Asn His Leu Phe Arg Gln Pro Ser
        675                 680                 685
Asn Ser Pro Pro Met Ser Ser Ala Met Ile Gln Pro His Gly Ala
690                 695                 700
Ala Ser Ser Ser Gln Phe Gln Gly Leu Pro Ser Arg Ser Ala Ile Phe
705                 710                 715                 720
Gln Gln Gln Pro Glu Asn Cys Ser Ser Pro Pro Asn Val Ala Leu Thr
                725                 730                 735
Cys Leu Gly Met Gln Gln Pro Ala Gln Ser Gln Gln Val Thr Ile Gln
        740                 745                 750
Val Gln Glu Pro Val Asp Met Leu Ser Asn Met Pro Gly Thr Ala Ala
        755                 760                 765
Gly Ser Ser Gly Arg Gly Ile Ser Ile Ser Pro Ser Ala Gly Gln Met
770                 775                 780
Gln Met Gln His Arg Thr Asn Leu Met Ala Thr Leu Ser Tyr Gly His
785                 790                 795                 800
Arg Pro Leu Ser Lys Gln Leu Ser Ala Asp Ser Ala Glu Ala His Ser
                805                 810                 815
Leu Asn Val Asn Arg Phe Ser Pro Ala Asn Tyr Asp Gln Ala His Leu
                820                 825                 830
His Pro His Leu Phe Ser Asp Gln Ser Arg Gly Ser Pro Ser Ser Tyr
        835                 840                 845
Ser Pro Ser Thr Gly Val Gly Phe Ser Pro Thr Gln Ala Leu Lys Val
        850                 855                 860
Pro Pro Leu Asp Gln Phe Pro Thr Phe Pro Pro Ser Ala His Gln Gln
865                 870                 875                 880
Pro Pro His Tyr Thr Thr Ser Ala Leu Gln Gln Ala Leu Leu Ser Pro
                885                 890                 895
Thr Pro Pro Asp Tyr Thr Arg His Gln Gln Val Pro His Ile Leu Gln
                900                 905                 910
Gly Leu Leu Ser Pro Arg His Ser Leu Thr Gly His Ser Asp Ile Arg
        915                 920                 925
Leu Pro Pro Thr Glu Phe Ala Gln Leu Ile Lys Arg Gln Gln Gln Gln
930                 935                 940
Arg Gln Gln Gln Gln Gln Gln Gln Gln Glu Tyr Gln Glu Leu
945                 950                 955                 960
Phe Arg His Met Asn Gln Gly Asp Ala Gly Ser Leu Ala Pro Ser Leu
                965                 970                 975
Gly Gly Gln Ser Met Thr Glu Arg Gln Ala Leu Ser Tyr Gln Asn Ala
        980                 985                 990
Asp Ser Tyr His His His Thr Ser  Pro Gln His Leu Leu  Gln Ile Arg
        995                 1000                1005
Ala Gln  Glu Cys Val Ser Gln  Ala Ser Ser Pro Thr  Pro Pro His
   1010                 1015                 1020
```

-continued

```
Gly Tyr Ala His Gln Pro Ala Leu Met His Ser Glu Ser Met Glu
    1025                1030                1035

Glu Asp Cys Ser Cys Glu Gly Ala Lys Asp Gly Phe Gln Asp Ser
    1040                1045                1050

Lys Ser Ser Ser Thr Leu Thr Lys Gly Cys His Asp Ser Pro Leu
    1055                1060                1065

Leu Leu Ser Thr Gly Gly Pro Gly Asp Pro Glu Ser Leu Leu Gly
    1070                1075                1080

Thr Val Ser His Ala Gln Glu Leu Gly Ile His Pro Tyr Gly His
    1085                1090                1095

Gln Pro Thr Ala Ala Phe Ser Lys Asn Lys Val Pro Ser Arg Glu
    1100                1105                1110

Pro Val Ile Gly Asn Cys Met Asp Arg Ser Ser Pro Gly Gln Ala
    1115                1120                1125

Val Glu Leu Pro Asp His Asn Gly Leu Gly Tyr Pro Ala Arg Pro
    1130                1135                1140

Ser Val His Glu His His Arg Pro Arg Ala Leu Gln Arg His His
    1145                1150                1155

Thr Ile Gln Asn Ser Asp Asp Ala Tyr Val Gln Leu Asp Asn Leu
    1160                1165                1170

Pro Gly Met Ser Leu Val Ala Gly Lys Ala Leu Ser Ser Ala Arg
    1175                1180                1185

Met Ser Asp Ala Val Leu Ser Gln Ser Ser Leu Met Gly Ser Gln
    1190                1195                1200

Gln Phe Gln Asp Gly Glu Asn Glu Glu Cys Gly Ala Ser Leu Gly
    1205                1210                1215

Gly His Glu His Pro Asp Leu Ser Asp Gly Ser Gln His Leu Asn
    1220                1225                1230

Ser Ser Cys Tyr Pro Ser Thr Cys Ile Thr Asp Ile Leu Leu Ser
    1235                1240                1245

Tyr Lys His Pro Glu Val Ser Phe Ser Met Glu Gln Ala Gly Val
    1250                1255                1260
```

<210> SEQ ID NO 3
<211> LENGTH: 158
<212> TYPE: PRT
<213> ORGANISM: Homo sapiens

<400> SEQUENCE: 3

```
Gln Glu Tyr Gln Glu Leu Phe Arg His Met Asn Gln Gly Asp Ala Gly
1               5                   10                  15

Ser Leu Ala Pro Ser Leu Gly Gly Gln Ser Met Thr Glu Arg Gln Ala
            20                  25                  30

Leu Ser Tyr Gln Asn Ala Asp Ser Tyr His His Thr Ser Pro Gln
        35                  40                  45

His Leu Leu Gln Ile Arg Ala Gln Glu Cys Val Ser Gln Ala Ser Ser
    50                  55                  60

Pro Thr Pro Pro His Gly Tyr Ala His Gln Pro Ala Leu Met His Ser
65                  70                  75                  80

Glu Ser Met Glu Glu Asp Cys Ser Cys Glu Gly Ala Lys Asp Gly Phe
                85                  90                  95

Gln Asp Ser Lys Ser Ser Ser Thr Leu Thr Lys Gly Cys His Asp Ser
            100                 105                 110

Pro Leu Leu Leu Ser Thr Gly Gly Pro Gly Asp Pro Glu Ser Leu Leu
        115                 120                 125
```

Gly Thr Val Ser His Ala Gln Glu Leu Gly Ile His Pro Tyr Gly His
            130                 135                 140

Gln Pro Thr Ala Ala Phe Ser Lys Asn Lys Val Pro Ser Arg
145                 150                 155

<210> SEQ ID NO 4
<211> LENGTH: 474
<212> TYPE: DNA
<213> ORGANISM: Homo sapiens

<400> SEQUENCE: 4

```
caagaatacc aggaactgtt caggcacatg aaccaagggg atgcggggag tctggctccc      60
agccttgggg gacagagcat gacagagcgc caggctttat cttatcaaaa tgctgactct     120
tatcaccatc acaccagccc ccagcatctg ctacaaatca gggcacaaga atgtgtctca     180
caggcttcct cacccacccc gccccacggg tatgctcacc agccggcact gatgcattca     240
gagagcatgg aggaggactg ctcgtgtgag ggggccaagg atggcttcca agacagtaag     300
agttcaagta cattgaccaa aggttgccat gacagccctc tgctcttgag taccggtgga     360
cctggggacc ctgaatcttt gctaggaact gtgagtcatg cccaagaatt ggggatacat     420
ccctatggtc atcagccaac tgctgcattc agtaaaaata aggtgcccag caga           474
```

<210> SEQ ID NO 5
<211> LENGTH: 7
<212> TYPE: PRT
<213> ORGANISM: Homo sapiens

<400> SEQUENCE: 5

Thr Pro His Gly Tyr Ala His
1               5

<210> SEQ ID NO 6
<211> LENGTH: 36
<212> TYPE: DNA
<213> ORGANISM: Homo sapiens

<400> SEQUENCE: 6

```
gcttcctcac ccaccccgca gccggcactg atgcat                                36
```

<210> SEQ ID NO 7
<211> LENGTH: 36
<212> TYPE: DNA
<213> ORGANISM: Homo sapiens

<400> SEQUENCE: 7

```
atgcatcagt gccggctgcg gggtgggtga ggaagc                                36
```

<210> SEQ ID NO 8
<211> LENGTH: 7
<212> TYPE: PRT
<213> ORGANISM: Homo sapiens

<400> SEQUENCE: 8

Gln Pro His His Tyr Ser Leu
1               5

<210> SEQ ID NO 9
<211> LENGTH: 7
<212> TYPE: PRT
<213> ORGANISM: Homo sapiens

<400> SEQUENCE: 9

```
Asn Pro His Ser Tyr Pro His
1               5

<210> SEQ ID NO 10
<211> LENGTH: 7
<212> TYPE: PRT
<213> ORGANISM: Homo sapiens

<400> SEQUENCE: 10

Gln Pro His His Tyr Pro Leu
1               5

<210> SEQ ID NO 11
<211> LENGTH: 7
<212> TYPE: PRT
<213> ORGANISM: Homo sapiens

<400> SEQUENCE: 11

Ser Pro His His Tyr Pro His
1               5

<210> SEQ ID NO 12
<211> LENGTH: 7
<212> TYPE: PRT
<213> ORGANISM: Homo sapiens

<400> SEQUENCE: 12

Thr Pro His His Tyr Met His
1               5

<210> SEQ ID NO 13
<211> LENGTH: 7
<212> TYPE: PRT
<213> ORGANISM: Homo sapiens

<400> SEQUENCE: 13

Val Pro His Ser Tyr Pro His
1               5

<210> SEQ ID NO 14
<211> LENGTH: 7
<212> TYPE: PRT
<213> ORGANISM: Homo sapiens

<400> SEQUENCE: 14

Gln Pro His His Tyr Phe Lys
1               5

<210> SEQ ID NO 15
<211> LENGTH: 7
<212> TYPE: PRT
<213> ORGANISM: Homo sapiens

<400> SEQUENCE: 15

Trp Pro His His Phe Pro His
1               5

<210> SEQ ID NO 16
<211> LENGTH: 7
<212> TYPE: PRT
<213> ORGANISM: Homo sapiens

<400> SEQUENCE: 16

Val Pro His Gly Tyr Phe Leu
1               5
```

```
<210> SEQ ID NO 17
<211> LENGTH: 7
<212> TYPE: PRT
<213> ORGANISM: Homo sapiens

<400> SEQUENCE: 17

Thr Pro His Gly Tyr Ala His
1               5

<210> SEQ ID NO 18
<211> LENGTH: 7
<212> TYPE: PRT
<213> ORGANISM: Homo sapiens

<400> SEQUENCE: 18

Val Pro His Ser Tyr Pro His
1               5

<210> SEQ ID NO 19
<211> LENGTH: 7
<212> TYPE: PRT
<213> ORGANISM: Homo sapiens

<400> SEQUENCE: 19

Gln Pro His His Tyr Pro Phe
1               5

<210> SEQ ID NO 20
<211> LENGTH: 7
<212> TYPE: PRT
<213> ORGANISM: Homo sapiens

<400> SEQUENCE: 20

Ala Pro His His Tyr Pro Met
1               5

<210> SEQ ID NO 21
<211> LENGTH: 7
<212> TYPE: PRT
<213> ORGANISM: Homo sapiens

<400> SEQUENCE: 21

Leu Ala Ile Asn Ile Lys Ser
1               5

<210> SEQ ID NO 22
<211> LENGTH: 7
<212> TYPE: PRT
<213> ORGANISM: Homo sapiens

<400> SEQUENCE: 22

Ser Pro His Ser Tyr Pro Arg
1               5

<210> SEQ ID NO 23
<211> LENGTH: 28
<212> TYPE: DNA
<213> ORGANISM: Homo sapiens

<400> SEQUENCE: 23
cgggaattct ctcagcaaca tgccaggc                                28

<210> SEQ ID NO 24
<211> LENGTH: 27
<212> TYPE: DNA
```

```
<213> ORGANISM: Homo sapiens

<400> SEQUENCE: 24
aatgaattct cagttgatta gggcaga                                           27

<210> SEQ ID NO 25
<211> LENGTH: 36
<212> TYPE: DNA
<213> ORGANISM: Homo sapiens

<400> SEQUENCE: 25
cgccagtgtg ctggaattct gctgtccggc gcgagc                                 36

<210> SEQ ID NO 26
<211> LENGTH: 39
<212> TYPE: DNA
<213> ORGANISM: Homo sapiens

<400> SEQUENCE: 26
gcatgctcga gcggccgctt acacgcctgc ctgctccat                              39

<210> SEQ ID NO 27
<211> LENGTH: 58
<212> TYPE: DNA
<213> ORGANISM: Homo sapiens

<400> SEQUENCE: 27
ccgggccagg ctttatctta tcaaactcga gtttgataag ataaagcctg gcttttg          58
```